(12) United States Patent
Anderson et al.

(10) Patent No.: US 10,815,513 B2
(45) Date of Patent: Oct. 27, 2020

(54) FERMENTATION METHODS FOR PRODUCING STEVIOL GLYCOSIDES USING HIGH PH AND COMPOSITIONS OBTAINED THEREFROM

(71) Applicants: CARGILL, INCORPORATED, Wayzata, MN (US); EVOLVA, S.A., Reinach (CH)

(72) Inventors: James C. Anderson, Eden Prairie, MN (US); Manuel Quiros Asensio, Soborg (DK); Simon Carlsen, Copenhagen (DK); Ting Liu Carlson, Marietta, SC (US); Veronique Douchin, Birkerod (DK); Ariene M. Fosmer, Eden Prairie, MN (US); Hans Peter Smits, Holte (DK)

(73) Assignees: Cargill, Incorporated, Wayzata, MN (US); Evolva S.A., Reinach (CH)

( * ) Notice: Subject to any disclaimer, the term of this patent is extended or adjusted under 35 U.S.C. 154(b) by 0 days.

(21) Appl. No.: 15/578,125

(22) PCT Filed: May 27, 2016

(86) PCT No.: PCT/US2016/034728
§ 371 (c)(1),
(2) Date: Nov. 29, 2017

(87) PCT Pub. No.: WO2016/196321
PCT Pub. Date: Dec. 8, 2016

(65) Prior Publication Data
US 2018/0155751 A1  Jun. 7, 2018

Related U.S. Application Data

(60) Provisional application No. 62/168,345, filed on May 29, 2015.

(51) Int. Cl.
| | | |
|---|---|---|
| C12P 19/56 | (2006.01) | |
| C07H 15/256 | (2006.01) | |
| A23L 27/30 | (2016.01) | |

(52) U.S. Cl.
CPC .............. *C12P 19/56* (2013.01); *A23L 27/36* (2016.08); *C07H 15/256* (2013.01); *A23V 2002/00* (2013.01)

(58) Field of Classification Search
CPC ........ A23L 27/36; C07H 15/256; C12P 19/56
See application file for complete search history.

(56) References Cited

U.S. PATENT DOCUMENTS

| | | |
|---|---|---|
| 2002/0164700 A1 | 11/2002 | Andersen et al. |
| 2006/0083838 A1 | 4/2006 | Jackson et al. |
| (Continued) | | |

FOREIGN PATENT DOCUMENTS

| | | | |
|---|---|---|---|
| EP | 1305440 | 6/2010 | |
| WO | WO-0125467 A1 * | 4/2001 | ............... C12N 1/16 |
| (Continued) | | | |

OTHER PUBLICATIONS

Chisti, Y. "Fermentation (Industrial): Basic Considerations" in: "Encyclopedia of Food Microbiology" (1999 ed.), pp. 663-674.*
(Continued)

*Primary Examiner* — Nikki H. Dees
*Assistant Examiner* — Changqing Li
(74) *Attorney, Agent, or Firm* — McDonnell Boehnen Hulbert & Berghoff LLP

(57) ABSTRACT

Disclosed are methods for producing steviol glycosides, such as rebaudioside D and rebaudioside M, using engineered yeast. In some embodiments, the methods include fermenting with a yeast at a high pH such as of about 5.8 or greater. In some embodiments, the methods can be carried
(Continued)

out by first growing the yeast at a lower first pH, and then adjusting the pH to a higher pH.

21 Claims, 4 Drawing Sheets

Specification includes a Sequence Listing.

(56) References Cited

U.S. PATENT DOCUMENTS

| | | | |
|---|---|---|---|
| 2006/0134742 | A1 | 6/2006 | Brazeau et al. |
| 2010/0184133 | A1 | 7/2010 | Norgaard et al. |
| 2011/0081697 | A1 | 4/2011 | Liu et al. |
| 2011/0189717 | A1 | 8/2011 | Ajikumar et al. |
| 2012/0164678 | A1 | 6/2012 | Stephanopoulos et al. |
| 2012/0165562 | A1* | 6/2012 | Hattendorf ....... C12Y 102/0105 554/1 |
| 2013/0071339 | A1 | 3/2013 | Markosyan et al. |
| 2013/0171328 | A1* | 7/2013 | Kishore ............ C12N 15/8243 426/658 |
| 2014/0329281 | A1 | 11/2014 | Houghton-Larsen et al. |
| 2014/0357588 | A1 | 12/2014 | Markosyan et al. |
| 2015/0031868 | A1 | 1/2015 | Lehmann et al. |
| 2015/0037462 | A1 | 2/2015 | Markosyan et al. |
| 2016/0102331 | A1 | 4/2016 | Boer et al. |
| 2016/0153017 | A1 | 6/2016 | Van Der Hoeven et al. |
| 2016/0177360 | A1 | 6/2016 | Boer et al. |
| 2016/0348192 | A1* | 12/2016 | Tilloy ..................... C12R 1/865 |
| 2018/0073050 | A1 | 3/2018 | Boer et al. |
| 2018/0148750 | A1 | 5/2018 | Anderson et al. |
| 2018/0163244 | A1 | 6/2018 | Anderson et al. |
| 2018/0230504 | A1 | 8/2018 | Anderson et al. |

FOREIGN PATENT DOCUMENTS

| | | | |
|---|---|---|---|
| WO | WO2006045023 | | 4/2006 |
| WO | WO2009140394 | | 11/2009 |
| WO | WO2011153378 | | 12/2011 |
| WO | WO2013022989 | | 2/2013 |
| WO | WO2013096420 | | 6/2013 |
| WO | WO2013110673 | | 8/2013 |
| WO | 2014122227 | A2 | 8/2014 |
| WO | WO2014122328 | | 8/2014 |
| WO | WO2014145521 | | 9/2014 |
| WO | WO2014191580 | | 12/2014 |
| WO | WO2014191581 | | 12/2014 |
| WO | WO2014193888 | | 12/2014 |
| WO | WO2014193934 | | 12/2014 |
| WO | WO2015007748 | | 1/2015 |
| WO | WO2015011209 | | 1/2015 |
| WO | 2015014969 | A1 | 2/2015 |
| WO | WO2015014959 | | 2/2015 |
| WO | WO-2015014969 | A1 * | 2/2015 ............... A23L 2/02 |
| WO | WO2016196345 | | 12/2016 |
| WO | WO2016196368 | | 12/2016 |
| WO | WO2017024313 | | 2/2017 |

OTHER PUBLICATIONS

International Search Report of PCT/US2016/034728 dated Sep. 8, 2016 (4 pgs.).
"Nomenclature committee of the international union of biochemistry and molecular biology (NC-IUBMB), Enzyme Supplement 5 (1999)," Eur J Biochem. 264(2):610-50, (1999).
Anderlei et al., "Device for sterile online measurement of the oxygen transfer rate in shaking flasks," Biochemical Engineering Journal 3478:1-6, (2000).
Barrett, "Nomenclature Committee of the International Union of Biochemistry and Molecular Biology (NC-IUBMB). Enzyme nomenclature. Recommendations 1992. Supplement 2: corrections and additions (1994)," Eur. J. Biochem., 232:1-6, (1995).
Barrett, "Nomenclature Committee of the International Union of Biochemistry and Molecular Biology (NC-IUBMB). Enzyme nomenclature. Recommendations 1992. Supplement 3: corrections and additions (1995)," Eur J Biochem. 237(1):1-5, (1996).
Barrett, "Nomenclature Committee of the International Union of Biochemistry and Molecular Biology (NC-IUBMB). Enzyme Nomenclature. Recommendations 1992. Supplement 4: corrections and additions (1997)," Eur J Biochem. 250(1):1-6, (1997).
Chen et al., "The glucose RQ-feedback control leading to improved erythromycin production by a recombinant strain Saccharopolyspora erythraea ZL1004 and its scale-up to 372-m(3) fermenter," Bioprocess Biosyst Eng. 38(1):105-12 (2015).
Jasmin, et al., "The yield of experimental yeast populations declines during selection," Proc Biol Sci. 2012. vol. 279 (1746): p. 4382-8 (2012).
Jules, et al., "Two Distinct Pathways for Trehalose Assimilation in the Yeast *Saccaromyces cerevisiae*," Appl Environ C Microbiol., vol. 70(5), p. 2771-2778 (2004).
Li et al., "Phylogenetic analysis of the UDP-glycosyltransferase multigene family of *Arabidopsis thaliana*," J Biol Chem. 276(6):4338-43 (2001).
Lynd, et al., "Microbial cellulose utilization: fundamentals and biotechnology," Microbial. Mol. Biol. Rev., 66:506-577 (2002).
Ohta et al., "Characterization of Novel Steviol Glycosides from leaves of Stevia rebaudiana Morita", Journal of Applied Glycoscience, The Japanese Society of Applied Glycoscience, Aug. 17, 2010, Issue 57, pp. 199-209.
Prakash et al., "Isolation, characterization and sensory evaluation of a Hexa beta-D-glucopyranosyl diterpene from Stevia rebaudiana," Nat Prod Commun. 8(11):1523-6 (2013).
Prakash et al., "Catalytic hydrogenation of the sweet principles of Stevia rebaudiana, Rebaudioside B, Rebaudioside C, and Rebaudioside D and sensory evaluation of their reduced derivatives," Int J Mol Sci. 13(11):15126-36 (2012).
Tipton, "Nomenclature Committee of the International Union of Biochemistry and Molecular Biology (NC-IUBMB). Enzyme nomenclature. Recommendations 1992. Supplement: corrections and additions," Eur J Biochem., 223(1):1-5 (1994).
Verduyn, C. et al., "Effect of benzoic acid on metabolic fluxes in yeasts: a continuous-culture study on the regulation of respiration and alcoholic fermentation," Yeast 8, 501-517 (1992).
International Preliminary Report on Patentability from then International Search Authority for International Application No. PCT/US2016/034728; dated Dec. 5, 2017, pp. 1-14.
Kizer et al, "Application of functional genomics to pathway optimization for increased isoprenoid production," Appl Environ Microbiol.; 74(10):3229-41 (2008).
Sena et al., "Effects of high medium pH on growth, metabolism and transport in Saccharomyces cerevisiae," FEMS Yeast Research, vol. 15, No. 2, pp. 1-13 (2015).
Prather et al., "De novo biosynthetic pathways: rational design of microbial chemical factories," Curr Opin Biotechnol. 19(5):468-74 (2008).
Extended European Search Report and Opinion issued by the European Patent Office for European Application No. 16804137.4, dated Sep. 14, 2018 (pp. 1-8).
International Search Report issued by the International Searching Authority for International Application No. PCT/US2016/034781, dated Aug. 29, 2016 (2 pages).
International Preliminary Report on Patentability from then International Search Authority for International Application No. PCT/US2016/034781; dated Aug. 3, 2016, pp. 1-9.
International Preliminary Report on Patentability from then International Search Authority for International Application No. PCT/US201616/046072; dated Feb. 6, 2018, pp. 1-12.
Extended European Search Report and Opinion issued by the European Patent Office for European Application No. 16804152.3, dated Nov. 6, 2018 (pp. 1-4).
Supplementary European Search Report and Opinion issued by the European Patent Office for European Application No. 168041523, dated Oct. 25, 2018 (pp. 1-2).
International Search Report issued by the International Searching Authority for International Application No. PCT/US2016/034826, dated Sep. 13, 2016 (4 pages).

(56) References Cited

OTHER PUBLICATIONS

International Preliminary Report on Patentability from then International Search Authority for International Application No. PCT/US2016/034826; dated Aug. 20, 2017, pp. 1-13.
Extended European Search Report and Opinion issued by the European Patent Office for European Application No. 16804170.5, dated Dec. 10, 2018 (p. 1).
International Search Report issued by the International Searching Authority for International Application No. PCT/US201616/046072, dated Dec. 1, 2016 (4 pages).
Extended European Search Report and Opinion issued by the European Patent Office for European Application No. 16834005.7, dated Feb. 13, 2019 (p. 1-11).
Brandle & Telmer, "Steviol glycoside biosynthesis," Phytochemistry 68(14):1855-63 (2007).
Coelho, "Yarrowia lipolytica: An industrial workhorse," Current Research, Technology and Education Topics in Applied Microbiology and Microbial Biotechnology A. Méndez-Vilas (Ed.), 930-944 (2010).
Goncalves, "Yarrowia Lipolytica and Its Multiple Applications in the Biotechnological Industry," the Scientific World Journal, vol. 2014, 1-14 (2014).
Kebabci et al., "Comparison of three Yarrowia lipolytica strains for lipase production: NBRC 1658, IFO 1195, and a local strain" Turk J Biol, 36 (2012) 15-24 (2012).
Kumar et al., "A comprehensive analysis of fifteen genes of steviol glycosides biosynthesis pathway in Stevia rebaudiana (Bertoni)" Gene 492:276-84 (Epub Oct. 20, 2011).
Moeller et al., "Optimization of Citric Acid Production from Glucose by Yarrowia lipolytica," Eng. Life Sci, 7(5):504-511 (2007).
International Search Report and Written Opinion issued by the International Searching Authority for International Application No. PCT/EP2014/065858, dated Oct. 20, 2014 (12 pages).
Non-Final Office Action issued in U.S. Appl. No. 15/578,154; dated Jul. 16, 2019, pp. 1-12.
Non-Final Office Action issued in U.S. Appl. No. 15/578,179; dated Dec. 23, 2019, pp. 1-9.
Non-Final Office Action issued in U.S. Appl. No. 15/750,636; dated Apr. 18, 2019, pp. 1-8.
Final Office Action issued in U.S. Appl. No. 151750,636; dated Oct. 7, 2019, pp. 1-12.
International Preliminary Report on Patentability from the International Search Authority for International Application No. PCT/EP2014/065858, dated Jan. 1, 2016 (9 pages).
Examination Report issued by the European Patent Office for European Application No. 14741925.3, dated Mar. 14, 2017 (pp. 1-10).
Examination Report issued by the European Patent Office for European Application No. 14741925.3, dated Feb. 26, 2018 (pp. 1-3).
Non-Final Office Action issued in U.S. Appl. No. 14/906,497; dated Jul. 17, 2018 pp. 1-30.

* cited by examiner

FERMENTATION METHODS FOR PRODUCING STEVIOL GLYCOSIDES USING HIGH PH AND COMPOSITIONS OBTAINED THEREFROM

CROSS-REFERENCE TO RELATED APPLICATIONS

This application is a national phase application of PCT/US2016/034728, filed May 27, 2016, and entitled FERMENTATION METHODS FOR PRODUCING STEVIOL GLYCOSIDES USING HIGH PH AND COMPOSITIONS OBTAINED THEREFROM, which claims benefit of U.S. Provisional Patent Application No. 62/168,345 filed May 29, 2015, and entitled FERMENTATION METHODS FOR PRODUCING STEVIOL GLYCOSIDES USING HIGH PH AND COMPOSITIONS OBTAINED THEREFROM, each of which is hereby incorporated by reference in its entirety.

REFERENCE TO SEQUENCE LISTING

This application contains references to amino acid sequences and/or nucleic acid sequences which have been submitted concurrently herewith as an ASCII text file entitled "CAR0210WO_Sequence_Listing.txt," created on May 27, 2016, and having a size of 92 KB. The sequence listing is hereby incorporated by reference in its entirety pursuant to 37 C.F.R. § 1.52(e)(5).

FIELD

The present invention relates fermentation methods for producing steviol glycosides, fermentation compositions, and steviol glycoside compositions produced by fermentation.

BACKGROUND

Sugars, such as sucrose, fructose and glucose, are utilized to provide a pleasant taste to beverages, foods, pharmaceuticals, and oral hygienic/cosmetic products. Sucrose, in particular, imparts a taste preferred by consumers. Although sucrose provides superior sweetness characteristics, it is caloric. Non-caloric or lower caloric sweeteners have been introduced to satisfy consumer demand, and there is desire for these types of sweeteners that have favorable taste characteristics.

*Stevia* is a genus of about 240 species of herbs and shrubs in the sunflower family (Asteraceae), native to subtropical and tropical regions from western North America to South America. The species *Stevia rebaudiana*, commonly known as sweetleaf, sweet leaf, sugarleaf, or simply *stevia*, is widely grown for its sweet leaves. *Stevia*-based sweeteners may be obtained by extracting one or more sweet compounds from the leaves. Many of these compounds are steviol glycosides, which are glycosides of steviol, a diterpene compound. These diterpene glycosides are about 150 to 450 times sweeter than sugar. Steviol glycosides differ from each other by sweetness power as well as other sensory features contributing to taste quality such as bitterness, lingering aftertaste and the like. See Kinghorn, A. D., *Stevia*: The genus *Stevia*, Taylor & Francis, London (2002).

Examples of steviol glycosides are described in WO 2013/096420 (see, e.g., listing in FIG. 1); and in Ohta et. al., "Characterization of Novel Steviol Glycosides from Leaves of *Stevia rebaudiana* Morita," J. Appl. Glycosi., 57, 199-209 (2010) (See, e.g., Table 4 at p. 204). Structurally, the diterpene glycosides are characterized by a single base, steviol, and differ by the presence of carbohydrate residues at positions C13 and C19, as presented in FIGS. 2a-2k. See also PCT Patent Publication WO 2013/096420.

Typically, on a dry weight basis, the four major steviol glycosides found in the leaves of *Stevia* are dulcoside A (0.3%), rebaudioside C (0.6-1.0%), rebaudioside A (3.8%) and stevioside (9.1%). Other glycosides identified in *Stevia* extract include one or more of rebaudioside B, D, E, F, G, H, I, J, K, L, M, N, O, steviolbioside and rubusoside.

While the major steviol glycoside Reb A is commonly used as sweetener in beverage applications it has off-taste issues. More recently, there has been focus on certain minor steviol glycosides which have better taste properties. For example, rebaudioside M has higher sweetness intensity and is more potent than other steviol glycosides (e.g., see Prakash, I., et al. (2013) Nat. Prod. Commun., 8: 1523-1526, and WO 2013/096420). Rebaudioside D tastes about 200-220 times sweeter than sucrose and in a sensory evaluation it had a slow onset of sweetness and was very clean, namely sweeter overall than sucrose, less sweet lingering aftertaste compared to sucrose (e.g., see Prakash, I., et al. (2012) Int. J. Mol. Sci., 13:15126-15136).

Molecular techniques have been used to prepare recombinant organisms capable of synthesizing steviol glycosides via fermentation. For example, recombinant strains of *S. cerevisiae* having multiple transgenes encoding enzymes involved in steviol glycoside synthesis have been used for the production of rebaudioside M and rebaudioside D (see, for example, WO2014/122227).

SUMMARY

The present invention generally relates to methods for producing steviol glycosides using engineered yeast, as well as fermentation compositions, and fermentation products that include one or more steviol glycosides. Fermentation conditions of the disclosure can promote increased production of steviol glycosides from the engineered yeast, and can also provide desirable steviol glycoside ratios, such as fermentation compositions that have high rebaudioside D to rebaudioside M ratios. For example, in some embodiments of the invention, a fermentation composition may include a ratio of rebaudioside D to rebaudioside M of 1:20 or greater. In still other embodiments, the ratio of rebaudioside D to rebaudioside M is in the range of 1:20 to 1:1. In other embodiments, the ratio of rebaudioside D to rebaudioside M at a second pH is greater than a ratio of rebaudioside D to rebaudioside M produced when an engineered yeast is maintained at the first pH throughout fermentation.

In one embodiment, the invention provides a method for producing steviol glycoside which involves changing the medium to a higher pH condition during fermentation for production of the steviol glycoside(s).

The method includes a step of growing engineered yeast in a first medium at a first pH, wherein the engineered yeast are capable of producing one or more steviol glycoside(s). An "engineered yeast" refers to yeast cells having at least one exogenous DNA sequence that is introduced into the cell, either integrated into the cell's genome or present on an extrachromosomal construct, such as a plasmid or episome. Next, a composition is added to the first medium to provide a second medium having a second pH that is greater than the first pH. In the second medium the engineered yeast is fermented to produce the one or more steviol glycoside(s). The composition added to the medium can include a nitrogen-containing compound, such as one selected from ammonium hydroxide, urea, ammonium sulfate. The composition added to the medium can be used to control the pH. The pH can also be controlled by a non-nitrogen containing base, such as potassium hydroxide or sodium hydroxide or calcium hydroxide and supplementing the nitrogen in the medium with a yeast nitrogenous base, ammonium sulfate, urea, yeast extract or other nitrogen containing nutrients.

In the second medium, the pH can be adjusted to greater than about 5, greater than about 5.5, or greater than about 5.8, such as in the range of about 5.8 to 7.5 or 5.8 to 6.2. The nitrogen-containing compound added to the medium can be a base, such as ammonium hydroxide, and be used to form the second, higher, pH condition. Alternatively, a nitrogen-containing compound can be used with a non-nitrogen base to provide the higher pH. The nitrogen-containing compound, such as yeast extract, ammonium hydroxide, urea, ammonium sulfate, or combinations thereof, can be the predominant nitrogen component in the second medium during fermentation conditions. The non-nitrogen bases can include potassium hydroxide, sodium hydroxide, and calcium hydroxide.

An exemplary method involves (a) growing the engineered yeast in a medium having a carbohydrate (e.g., glucose) at a lower pH, such as below 5.8, and then (b) adding a composition with a nitrogen-containing compound, such as ammonium hydroxide, urea, ammonium sulfate, or combinations thereof, and optionally a non-nitrogen containing base, to the medium, along with additional carbohydrate, and optionally other fermentation compounds, to provide a medium having a pH of 5.8 or greater, and then fermenting the medium with the engineered yeast to produce steviol glycoside(s).

In another embodiment, the invention provides a method for producing steviol glycosides wherein a pH shift is not required, but rather optional. Accordingly, another embodiment is a method for producing steviol glycoside, where the method comprises a step of growing and fermenting a medium with an engineered yeast at a pH of 5.8 or greater in medium comprising a nitrogen source. The nitrogen source is selected from ammonium hydroxide, urea, and ammonium sulfate, yeast extract and one or a combination of these compounds is the primary nitrogen source during fermenting. During fermenting the engineered yeast produces one or more steviol glycoside(s). For example, the steviol glycosides include rebaudioside D, rebaudioside M or rebaudioside D and rebaudioside M. In some embodiments, the molar ratio of rebaudioside D to rebaudioside M is 1:20 or greater.

In another embodiment, the invention provides a method for increasing the production of a first, lower molecular weight steviol glycoside relative to a second, higher molecular weight steviol glycoside in an engineered yeast. The method includes a step of fermenting engineered yeast capable of producing one or more steviol glycoside(s) at a pH of 5.8 or greater in a fermentation medium, wherein the engineered yeast produces a ratio of the first and second steviol glycosides at pH of 5.8 or greater that is greater than a ratio of the first and second steviol glycosides produced at a pH that is less than 5.8. For example, the method can increase the ratio of the first and second steviol glycosides at pH of 5.8 or greater by about 10% or greater over the ratio when then engineered yeast are grown at the lower pH.

In another embodiment, the invention also provides compositions comprising steviol glycosides produced by a fermentation process. Accordingly, in another embodiment, the invention provides a composition obtained from a fermentation process comprising rebaudioside D and rebaudioside M, wherein the molar ratio rebaudioside D to rebaudioside M is 1:20 or greater.

DETAILED DESCRIPTION

Figure 1:
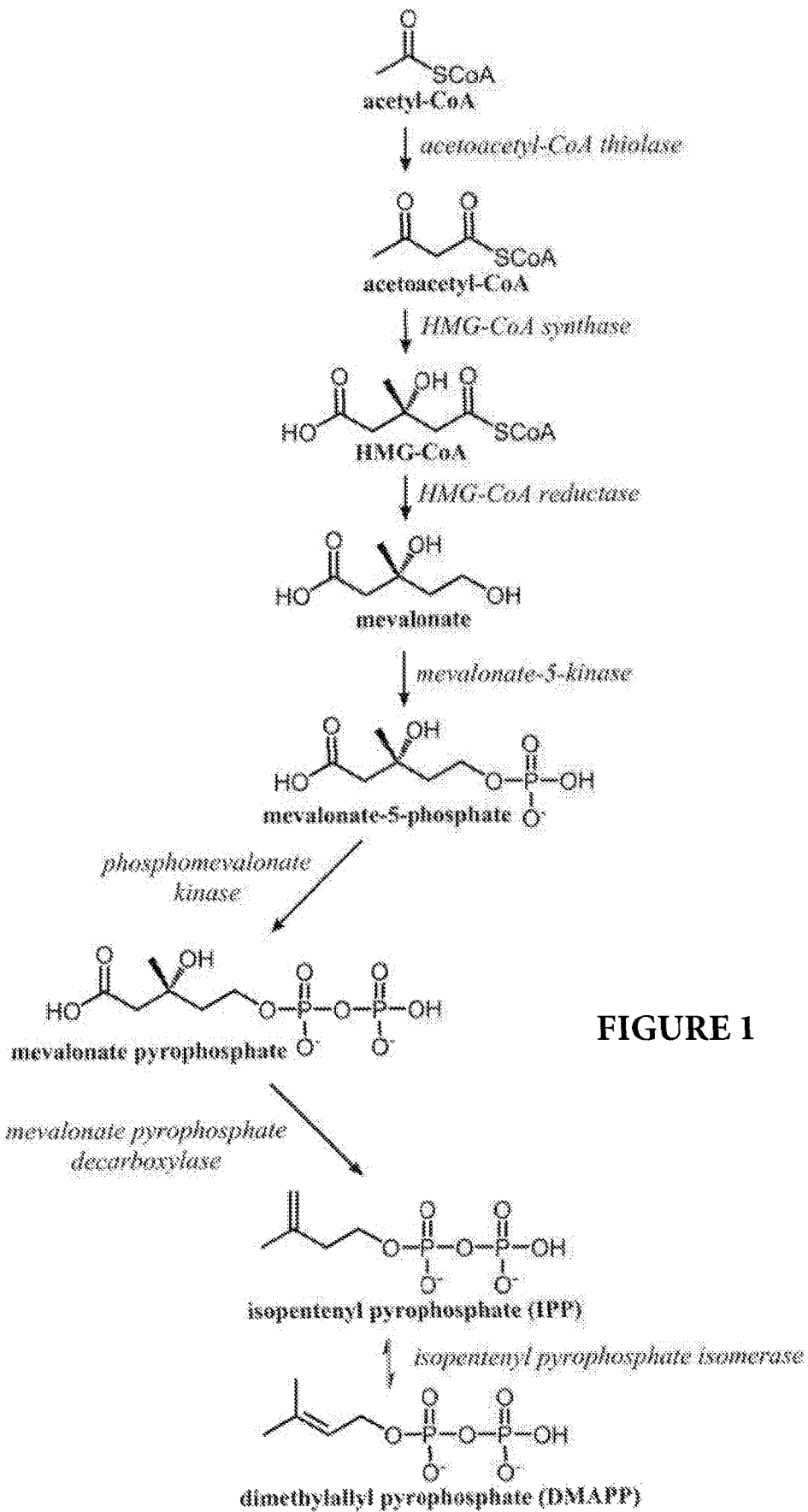
FIG. 1 shows a representative mevalonate pathway.

Embodiments of the disclosure described herein are not intended to be exhaustive or to limit the invention to the precise forms disclosed in the following detailed description. Rather a purpose of the embodiments chosen and described is so that the appreciation and understanding by others skilled in the art of the principles and practices of the present invention can be facilitated.

Fermentation methods of the disclosure use engineered yeast capable of producing steviol glycosides. The engineered yeast capable of producing steviol glycosides can include one or more exogenous nucleic acids that encode enzyme(s) that promote formation of one or more steviol glycosides in the cell. For example, the engineered yeast can have a set of enzymes that provide a pathway for the synthesis of the steviol glycosides RebM and RebD.

As used herein, the term "steviol glycoside(s)" refers to glycosides of steviol. Exemplary steviol glycoside, include, but not are not limited to, rebaudioside A, rebaudioside B, rebaudioside C, rebaudioside D, rebaudioside E, rebaudioside F, rebaudioside G, rebaudioside H, rebaudioside I, rebaudioside J, rebaudioside K, rebaudioside L, rebaudioside M, rebaudioside N, rebaudioside O, stevioside, steviolbioside, dulcoside A, rubusoside. Engineered yeast can produce steviol glycosides that are the same as steviol glycosides found in nature ("naturally occurring") as well as steviol glycosides that are not found in nature. Steviol glycosides can be formed in engineered yeast by enzymatic processes.

Structurally, steviol glycosides have a central molecular moiety, which is a single steviol base, and glucopyranosyl residues attached to the C13 and/or C19 atoms of the steviol base, according to the atom numbering on the base shown below. That is, glucopyranosyl residues represent groups $R_1$ and $R_2$ in the following formula:

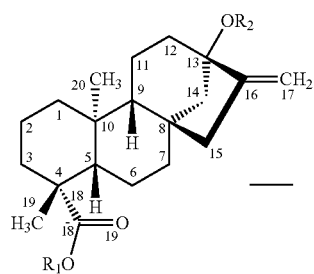

Table A below shows the various steviol glycosides and the corresponding $R_1$ and $R_2$ arrows:

TABLE A

| Compound name | $R_1$ (C-19) | $R_2$ (C-13) |
| --- | --- | --- |
| Steviol | H | H |
| Stevioside | β-Glu | β-Glu-β-Glu (2->1) |
| Rebaudioside A | β-Glu | β-Glu-β-Glu (2->1)<br>\|<br>β-Glu (3->1) |
| Rebaudioside B | H | β-Glu-β-Glu (2->1)<br>\|<br>β-Glu (3->1) |
| Rebaudioside C | β-Glu | β-Glu-α-Rha (2->1)<br>\|<br>β-Glu (3->1) |
| Rebaudioside D | β-Glu-β-Glu (2->1) | β-Glu-β-Glu (2->1)<br>\|<br>β-Glu (3->1) |
| Rebaudioside E | β-Glu-β-Glu (2->1) | β-Glu-β-Glu (2->1) |
| Rebaudioside G | β-Glu | β-Glu-β-Glu (3->1) |
| Rebaudioside M | β-Glu-β-Glu (2->1)<br>\|<br>β-Glu (3->1) | β-Glu-β-Glu (2->1)<br>\|<br>β-Glu (3->1) |
| Rebaudioside N | β-Glu-α-Rha (2->1)<br>\|<br>β-Glu (3->1) | β-Glu-β-Glu (2->1)<br>\|<br>β-Glu (3->1) |
| Rebaudioside O | β-Glu-α-Rha (2->1)-β-Glu (3->1)<br>\|<br>β-Glu (3->1) | β-Glu-β-Glu (2->1)<br>\|<br>β-Glu (3->1) |

Glu: glucose
Rha: rhamnose

According to the current disclosure, steviol glycosides are produced in a process that includes fermenting the engineered yeast at a pH that is higher than typical yeast fermentation conditions. By comparison, the yeast *Saccharomyces cerevisiae* is typically fermented at a pH in the range of 4 to 5.

The method of the disclosure can use various yeast host cells engineered to provide a pathway to one or more steviol glycosides. Such cells used in the methods of the disclosure can be transformed with one or more DNA construct(s) encoding enzymes for steviol glycoside synthesis. Exemplary yeast that can be used for hosts for exogenous DNA constructs encoding steviol glycoside pathway enzymes, include, but are not limited to species of *Candida, Kloeckera (Hanseniaspora), Kluyveromyces, Lipomyces, Pichia (Hansenula), Rhodotorula, Saccharomycete, Saccharomyces, Schizosaccharomyces, Torulopsis, Torulaspora, Yarrowia,* and *Zygosaccharomyces*. Exemplary species are *Candida albicans, Pichia pastoris, Saccharomyces cerevisiae,* and *Schizosaccharomyces pombe,* and *Yarrowia lipolytica*. Further, host cells can also include genetic modifications other than those of the steviol glycoside pathway that may provide improved performance during fermentation.

The term "exogenous" refers to a molecule, such as a nucleic acid, or an activity, such as an enzyme activity, that is introduced into the host yeast. An exogenous nucleic acid can be introduced into the yeast host by well-known techniques and can be maintained external to the hosts chromosomal material (e.g., maintained on a non-integrating vector), or can be integrated into the yeast's chromosome, such as by a recombination event. Generally, the genome of an engineered yeast is augmented through the stable introduction of one or more recombinant genes. An exogenous nucleic acid can encode an enzyme, or portion thereof, that is either homologous or heterologous to the yeast. An exogenous nucleic acid can be in the form of a "recombinant gene or DNA construct" referring to a nucleic acid that is in one or more ways manipulated through molecular techniques to be in a form that does not naturally exist.

The term "heterologous" (e.g., "non-native") refers to a molecule or activity that is from a source that is different than the referenced molecule or organism. Accordingly, a gene or protein that is heterologous to a referenced organism is a gene or protein not found in that organism. In the context of the disclosure, a "heterologous glycosyltransferase" refers to a glycosyltransferase polypeptide that is different from any glycosyltransferase polypeptide that may be native to the host organism. For example, a specific glycosyltransferase gene found in a first species and exogenously introduced into a host yeast organism that is different than the first species is "heterologous" to the host yeast.

The engineered yeast can use an auxotrophic marker suitable for selecting for a transformant having a nucleic acid encoding a steviol glycoside pathway enzyme. The host yeast can include modifications (deletions, etc.) in one or more genes that control auxotrophies, such as LYS2, LEU2, HIS3, URA3, URA5, and TRP1. Using a host cell having a desired genetic background for introduction of one or more exogenous genes, one or more gene construct(s) is introduced into a cell to integrate into the genome, or to be stably maintained and allow for expression. Methods for introducing a gene construct into a host cell include transformation, transduction, transfection, co-transfection, and electroporation. In particular, yeast transformation can be carried out using the lithium acetate method, the protoplast method, and the like. The gene construct to be introduced may be incorporated into a chromosome in the form of a plasmid, or by insertion into the gene of a host, or through homologous recombination with the gene of a host. The transformed yeast into which the gene construct has been introduced can be selected with a selectable marker (for example, an auxotrophic marker as mentioned above). Further confirmation can be made by measuring the activity of the expressed protein, or the production of a bioproduct associated with the introduced gene(s) such as a steviol glycoside.

The transformation of exogenous nucleic acid sequences including the steviol pathway genes can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of the introduced nucleic acid sequences or their corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

The terpenoid compounds isopentenyl diphosphate (IPP) and dimethylallyl diphosphate (DMAPP) can serve as chemical precursors to steviol glycosides in an engineered yeast. Some organisms, including plants, insect, and some microbial species, have a mevalonate (MVA) pathway that converts acetyl-CoA through a series of chemical intermediates to IPP and DMAPP. Some organisms produce IPP and DMAPP through the non-mevalonate pathway (also known as the methyl D-erythritol 4-phosphate or MEP pathway) starting with glyceraldehyde-3-phosphate (G3P) and pyruvate (PYR).

The yeast *Saccharomyces cerevisiae* naturally expresses genes of the mevalonate pathway. Mevalonate pathway genes that encode enzymes that include: (a1) acetoacetyl CoA thiolase (EC 2.3.1.9), (b1) 3-hydroxy-3-methylglutaryl-coenzyme A (HMG-CoA) synthase (EC 4.1.3.5); (c1) HMG-CoA reductase (EC 1.1.1.34); (d1) mevalonate kinase (EC 2.7.1.36); (e1) phosphomevalonate kinase (EC 2.7.4.2); and (f1) mevalonate diphosphate decarboxylase (EC 4.1.1.33). Enzymes of the mevalonate pathway converts acetyl-CoA to IPP as follows: acetyl-CoA→acetoacetyl-CoA→3-hydroxy-3-methylglutaryl-CoA→mevalonate-→mevalonate-5-phosphate→mevalonate-5-pyrophosphate→IPP. See also FIG. 1

In some embodiments, the engineered yeast can include one or more modifications to increase the flux from acetyl-CoA to IPP and/or DMAPP, thereby providing an increased pool of IPP and/or DMAPP for use in a pathway to steviol. The modifications can include, for example, increasing expression or activity of one or more mevalonate pathway enzymes (a1)-(f1), such as by placing a nucleic acid encoding an enzyme that is homologous or heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a higher level of enzymatic activity as compared to the native enzyme.

Alternatively, the non-mevalonate (MEP) pathway can be used to provide IPP and DMAPP as precursors to steviol glycoside production. The yeast *Saccharomyces cerevisiae* do not naturally express genes of the MEP pathway, but can optionally be engineered to provide MEP pathway genes. Theoretically, the MEP pathway is more energetically efficient generally because it loses less carbon as CO2 as compared to the MVA pathway (MEP pathway: 1 CO2/IPP; MVA pathway: 4 CO2/IPP; sugar as carbon source).

Figure 2:
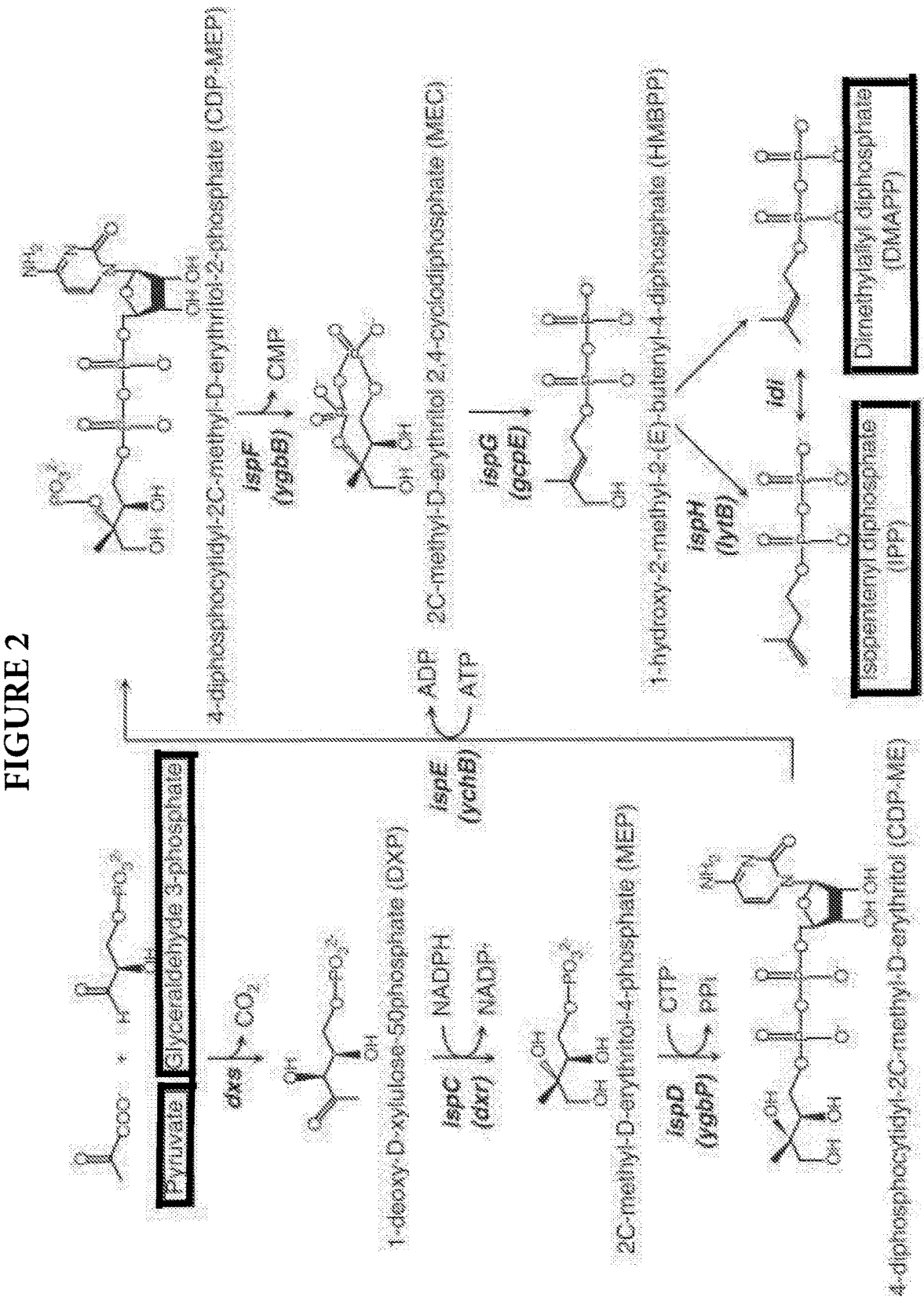
FIG. 2 shows a representative non-mevalonate pathway.

In particular, in the non-mevalonate (MEP) pathway compounds isopentenyl diphosphate (IPP), dimethylallyl diphosphate (DMAPP) are generated through a series of intermediates leading from glyceraldehydes-3-phosphate (G3P) and pyruvate (PYR), and a number of enzymes are responsible for this conversion. Enzymes involved in a biosynthetic pathway from G3P and PYR to IPP and DMAPP include (a2) l-deoxy-D-xylulose-5-phosphate synthase (DXS), (b2) 1-Deoxy-D-xylulose-5-phosphate reductoisomerase (ispC)-, (c2) 4-diphosphocytidyl-2C-methyl-D-erythritol synthase (IspD), (d2) 4-diphosphocytidyl-2-C-methyl-D-erythritol kinase (IspE), (e2) 2C-Methyl-D-erythritol-2,4-cyclodiphosphate Synthase (IspF), (f2) 1-hydroxy-2-methyl-2-(E)-butenyl-4-diphosphate synthase (IspG), (g2) 4-hydroxy-3-methyl-2-(E)-butenyl-4-diphosphate reductase (IspH), and (h2) isopentenyl-diphosphate isomerase (IDI), see FIG. 2.

The methods of the disclosure for producing steviol glycoside(s) by fermentation can use engineered yeast that have one or more genetic modifications to increase the flux from G3P and PYR to IPP and/or DMAPP, thereby providing an increased pool of IPP and/or DMAPP for use in a pathway to steviol. The modifications can include, for example, increasing expression or activity of one or more enzymes (a2)-(h2), such as by placing a nucleic acid encoding an enzyme that is heterologous to the yeast cell under the control of a promoter that provides increased expression, using multiple copies of the nucleic acid, and/or using a heterologous enzyme, a variant enzyme (e.g., one including one or more amino acid substitutions), or a variant heterologous enzyme that provides a high levels of enzymatic activity.

Figure 3:
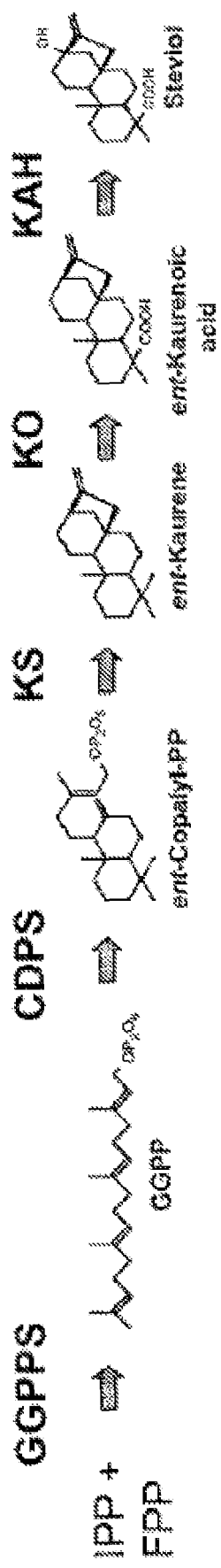
FIG. 3 shows a representative pathway for steviol production.

The methods of the disclosure for producing steviol glycoside(s) by fermentation can use engineered yeast can also include a pathway to convert IPP and/or DMAPP to steviol. For example, in some aspects the engineered yeast can include exogenous nucleic acids expressing the following enzymes: (a3) geranyl geranyldiphosphate synthase (GGPPS), (b3) copalyl diphosphate synthase (CDPS), (c3) kaurene synthase (KS), (d3) kaurene oxidase (KO), and (e3) kaurenoic acid 13-hydroxylase (KAH). Enzymes of the mevalonate pathway convert IPP and/or DMAPP to steviol as follows: IPP/DMAPP→geranyl geranyldiphosphate→copalyl diphosphate→kaurene→kaurenoic acid→steviol. (See FIG. 3) Exogenous nucleic acids encoding enzymes (a3)-(e3) that are heterologous to the yeast cell can be placed under the control of a promoter that provides increased expression, using multiple copies of the nucleic acid, and/or using a variant enzyme (e.g., one including one or more amino acid substitutions), or a variant heterologous enzyme that provides a high levels of enzymatic activity.

The methods of the disclosure for producing steviol glycoside(s) by fermentation can use engineered yeast having any pathway to convert steviol to a steviol glycoside. If more than one steviol glycoside pathway enzyme is present in the engineered yeast, the yeast may be able to produce different steviol glycosides. For example, the yeast may be able to produce two, three, four, five, six, seven, eight, nine, ten, or more than ten different steviol glycoside species.

Figure 4:
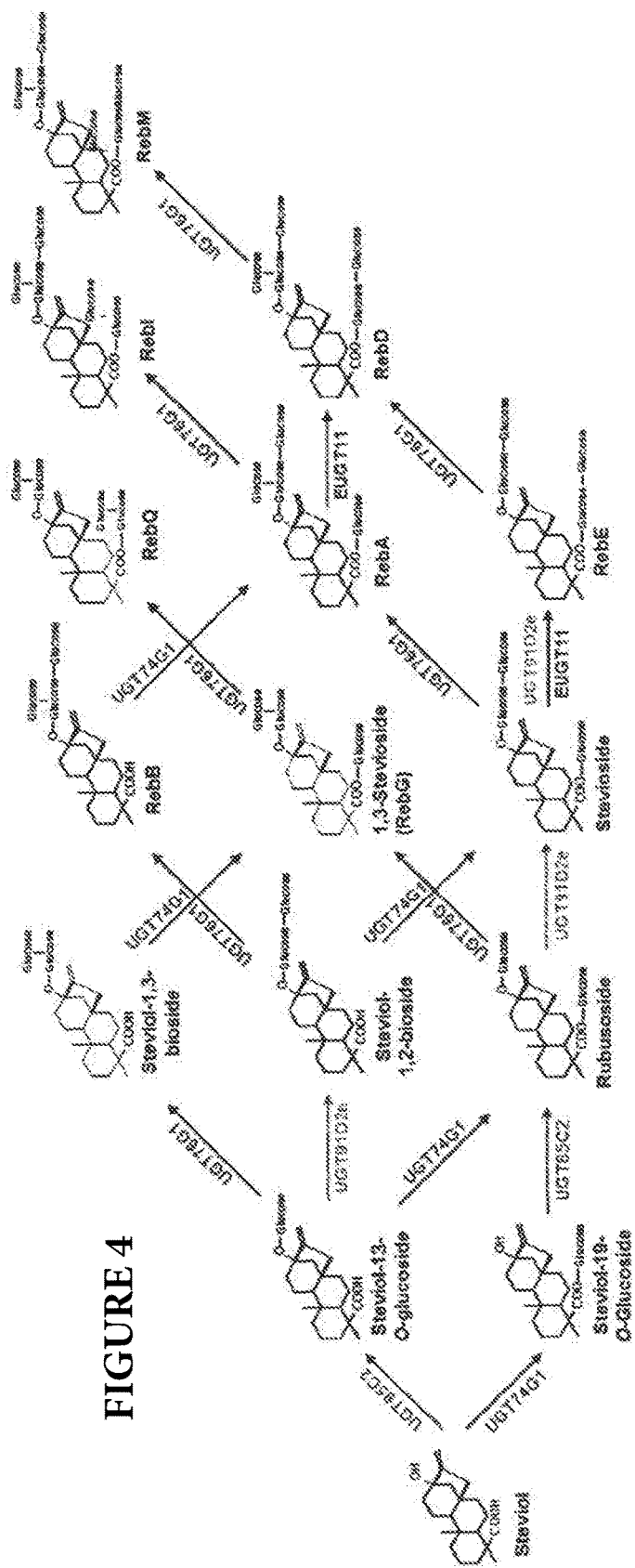
FIG. 4 shows representative pathways for the biosynthesis of steviol glycosides from steviol.

The steviol glycoside pathway can include one or more uridine diphosphate (UDP) glycosyltransferases (UGTs) that mediate the transfer of glycosyl residues from activated nucleotide sugars to acceptor molecules. In the case of a steviol glycoside pathway, a monosaccharide unit can be transferred to a hydroxyl or carboxyl moiety on a steviol or steviol glycoside molecule, or to a hydroxyl group on a glucose group that is attached to the steviol base. See FIG. 4 UGTs have been classified into families and subfamilies based on sequence homology. See Li, et al., 2001, J. Biol. Chem. 276:4338-4343. A superfamily of over 100 genes encoding UGTs, each containing a 42 amino acid consensus sequence, has been identified in the model plant *Arabidopsis thaliana*, and genes encoding UGTs have also been identified in several other higher plant species.

Exemplary UDP-glucosyltransferase can be any UDP-glucosyltransferase capable of adding at least one glucose unit to the steviol and or steviol glycoside substrate to provide the target steviol glycoside. In one embodiment, the engineered yeast can include one or more UDP-glucosyltransferase selected from group UGT74G1 (SEQ ID NO: 1), UGT85C2 (SEQ ID NO: 2), UGT76G1 (SEQ ID NO: 3), UGT91D2 (SEQ ID NO: 4), and also UGTs having substantial identity (e.g. >85%, >75%, >65%, >55%, >45% and >35%) to these polypeptides. An engineered yeast can include one or more exogenous nucleic acid molecule(s) that code for these UGTs.

The engineered yeast can also include one or more UGT and UDP-glucose recycling enzyme(s). An exemplary UDP-glucosyltransferase capable of adding at least one glucose unit to rubusoside to form stevioside is UGT91D2 (SEQ ID NO: 4). An exemplary UDP-glucosyltransferase capable of adding at least one glucose unit to stevioside to form rebaudioside A is UGT76G1 (SEQ ID NO: 3). An exemplary UDP-glucosyltransferase capable of adding at least one glucose unit to rebaudioside A to form rebaudioside D is UGT91D2 (SEQ ID NO: 4). An exemplary UDP-glucosyl-transferase capable of adding at least one glucose unit to rebaudioside D to form rebaudioside M is UGT76G1 (SEQ ID NO: 3).

Exemplary publications that describe engineered microorganisms for steviol glycoside production and steviol glycoside pathway enzymes include, for example, US2014/0357588, WO2014/193934, WO2014/193888, and WO2014/122227, each of which is incorporated herein by reference in their entirety.

In one embodiment, an engineered yeast useful for the production of steviol glycosides expresses the following enzymes: geranylgeranyl diphosphate synthase (GGPPS), ent-copalyl diphosphate synthase (CDPS), kaurene oxidase (KO), kaurene synthase (KS); steviol synthase (KAH), cytochrome P450 reductase (CPR), UGT74G1, UGT76G1, UGT91D2, UGT85C2 and a EUGT11. WO2014/122227 describes an engineered yeast strain that express these enzymes. The UDP-glucosyltransferases can be a gene encoding a polypeptide for example, UGT74G1 (SEQ ID NO: 1), UGT85C2 (SEQ ID NO: 2), UGT76G1 (SEQ ID NO: 3), UGT91D2 (SEQ ID NO: 4), and a EUGT11 (SEQ ID NO: 13); these genes encode polypeptides capable of carrying out a number of reactions such as a) a gene encoding a polypeptide capable of beta 1,2 glycosylation of the CT of the 19-O glucose of a steviol glycoside; (b) a gene encoding a polypeptide capable of beta 1,2 glycosylation of the C2' of the 13-O-glucose of a steviol glycoside; (c) a gene encoding a polypeptide capable of beta 1,3 glycosylation of the C3' of the 19-O-glucose of a steviol glycoside; (d) a gene encoding a polypeptide capable of beta 1,3 glucosylation of the C3' of the 13-O-glucose of a steviol glycoside; (i) a gene encoding a polypeptide capable of glucosylation of the 13-OH of steviol or a steviol glycoside; (j) a gene encoding a polypeptide capable of glucosylation of the C-19 carboxyl of steviol or a steviol glycoside. For example, UGT85C2 carries out reaction (i); UGT74G1 carries out reaction (j); UGT91D2 carries out reactions (a; weakly), (b); UGT76G1 carries out reactions (c) and (d) EUGT11 carries out reactions (a), (b; less well).

Aspects of the disclosure can be described with reference to stages of cell culture. For example, the process may include one or more "stages" or "phases" of culturing the engineered yeast. For example, the process can include a "seed/growth phase". As used herein "seed phase" refers to a period during which the cells are grown in a medium to become acclimated to the medium components (carbohydrates, nitrogen source, salts, vitamins, trace metals) that will be used in the subsequent growth phase and to increase cell numbers. "Growth phase" as used herein refers to the period during which the cells multiply (e.g. exponentially). During the seed/growth phase, the engineered yeast can begin to multiply by budding, referred to as yeast division.

The seed/growth phase can be characterized by rapid multiplication of the engineered yeast. The seed/growth phase can be described in terms of the doubling times of the engineered yeast. In some embodiments of the disclosure, growth of the engineered yeast can be performed at a lower (first) pH (e.g., about 5.8 or below or about 5.0 or below), and then at a time later in the growth phase, or at time in the subsequent fermentation phase, the pH can be increased to a higher (second) pH (e.g., about 5.8 or greater or about 6.0 or greater). In other embodiments of the disclosure, growth of the engineered yeast can be performed at the higher (second) pH, and therefore an adjustment to a higher pH during the growth and fermentation phases is not required.

After the growth phase, the engineered yeast can enter a "fermentation phase" in which growth has at least slowed and the engineered yeast are actively assimilating carbohydrate and producing the desired product, e.g., steviol glycoside(s). As used herein "fermentation," "fermenting," or variants therefor is used to describe the phase of significant production of steviol glycoside(s) by converting a substrate with a yeast, which can occur in partially aerobic, aerobic or anaerobic conditions. In partially aerobic conditions, both fermentative and respiratory pathways can be active, and some cell growth may occur. In partially aerobic conditions the amount of oxygen consumed can be less than during the seed/growth phase. As used herein, the phrase "throughout the process" or "throughout" when used in reference to the various phases or treatments means from growth phase through formation of product.

In some modes of practice, the pH of the medium during the fermentation phase can be at the higher pH if the pH of the medium was increased during, or at the beginning of the growth phase. In other modes of practice, the pH can be adjusted to the higher pH at a predetermined point during the fermentation phase. If the pH is increased during fermentation, it is preferably increased closer to the beginning of the fermentation phase than the end of the fermentation phase, and more preferably at the beginning or very close to the beginning of the fermentation phase.

In some modes of practice, the pH of the medium during the growth phase is carried out at the same pH as the fermentation phase. For example, the growth phase is carried out at the higher (second) pH. For example, the higher (second) pH is from about 5.8 or greater.

In some embodiments, the method of the disclosure for producing steviol glycoside(s) involves altering the medium in which the engineered cells are in to a higher pH for fermentation and production of steviol glycoside(s). Therefore, a step in the method can involve growing the engineered yeast in a first medium at a first, lower pH (e.g., pH 5.8 or less or pH 5.0 or less) and then after a period of time at the first, lower, pH the engineered yeast are fermented in a medium at a second pH that is higher than the first pH. The engineered yeast are fermented at the second, higher, pH (e.g., pH 5.8 or greater, or pH 6.0 or greater) to produce the one or more steviol glycoside(s), and the higher pH conditions can result in increased amounts of steviol glycosides, as well as a shift to more desirable ratios of steviol glycosides among those produced.

The term "medium" refers to a liquid composition in which the engineered yeast can be maintained, can grow, can be fermented, or combinations thereof. A "medium" may also be referred to as a "broth" or "cell culture," and terms such as "starting" or "fermentation" may be used to more specifically define the medium and the cellular activity that is occurring therein. A medium can be defined with regards to the components present in the medium, and amounts thereof, such as carbon sources, including (a) carbohydrates such as glucose and starch products such as maltodextrin; (b) nitrogen sources, such as yeast nitrogen base, ammonium hydroxide, urea, ammonium sulfate, yeast extract or any combination thereof; (c) salts, such as potassium phosphate (monobasic, dibasic), magnesium sulfate, sodium chloride, and calcium chloride; (d) vitamins, such as biotin, calcium pantothenate, folic acid, (myo)-inositol, nicotinic acid, p-aminobenzoic acid, pyridoxine HCl, riboflavin, thiamine HCl, and citric acid; (e) trace metals such as boric acid, copper sulfate, cobalt chloride, calcium chloride, potassium iodide, ferric chloride, magnesium sulfate, manganese chloride, sodium molybdate, and zinc sulfate. Components in the medium can be defined on a dry weight basis. Further, the medium is water-based, or an "aqueous" composition. The medium can also be defined with regards to its pH, and biocompatible acids, bases, and buffers that are used to control the pH in the medium.

Fermentation of the engineered yeast can be performed using a medium that has a starch and/or sugar containing plant material derivable from any plant and plant part, such as tubers, roots, stems, leaves and seeds. Starch and/or sugar-containing plant materials can be obtained from cereal, such as barley, wheat, maize, rye, sorghum, millet, barley, potatoes, cassava, or rice, and any combination thereof. The starch- and/or sugar-containing plant material can be processed, such as by methods such as milling, malting, or partially malting. In some embodiments, medium (with higher pH or lower pH) includes a treated starch. For example, the medium for growth and/or fermentation can include a partially hydrolyzed starch. The partially hydrolyzed starch can include high molecular weight dextrins and high molecular weight maltodextrins. A partially hydrolyzed starch product can be used that has amounts of starch and starch degradation products within desired ranges beneficial for steviol glycoside production.

Optionally, a starch degrading enzyme can be added to the medium that includes a starch material in order to increase the concentration of monomeric sugars such as glucose that can be utilized by the engineered yeast. Exemplary starch-degrading enzymes include amylolytic enzymes such as glycoamylase and amylase.

In some modes of practice, fermentation can be carried out in medium that includes steviol-containing compounds. Such compounds can be directly used by the glucosyltransferases in the engineered yeast. For example, optionally, fermentation can be carried out in medium containing steviol, steviol-13-O-glucoside or steviol-19-O-glucoside. Using this medium, the microorganism may contain and express genes encoding a functional EUGT11 (SEQ ID NO: 13), a functional UGT74G1 (SEQ ID NO: 1), a functional UGT85C2 (SEQ ID NO: 2), a functional UGT76G1 (SEQ ID NO: 3), and a functional UGT91D2 (SEQ ID NO: 4). Compounds such as rebaudioside A, rebaudioside D, and rebaudioside M may be obtained from the fermentation medium. As another option, fermentation can be carried out in medium containing rubusoside. Using this medium, the microorganism may contain and express genes encoding a functional EUGT11 (SEQ ID NO: 13), a functional UGT76G1 (SEQ ID NO: 3), and a functional UGT91D2 (SEQ ID NO: 4). Compounds such as rebaudioside A, D, and M may be obtained from the medium following fermentation. The terms "rebaudioside DM", "Reb DM", and variations thereof, as used herein, refer to glycosides that are primarily rebaudioside D and rebaudioside M (hence, the "DM"), their related isomers (e.g. natural or synthetic), and/or salts thereof. This terminology format may be used for glycosides having any other combination of glycosides, for example, but not limited to Reb DA, Reb MA, Reb DMA and the like.

In some cases fermentation is carried out in industrial capacity fermenters in order to achieve commercial scale economic benefits and control. In an embodiment, the fermentation is carried out in a fermenter that has a capacity of about 10,000 liters or more.

The terms "first medium" and "second medium" (and optionally, "third," "fourth," fifth," etc., if necessary) may be used to describe aspects of the method of producing steviol glycosides. In one mode of practice, a first medium at a lower pH (e.g., less than 5.8 or less than 5.0) and containing the engineered cells is provided and engineered yeast therein are cultured for a period of time. Subsequently, a liquid composition free of cells (e.g., a "feed composition") is added to the first medium to provide a second medium having the same or a higher pH, which can be used for fermentation of the engineered yeast. The feed composition can be added to the first medium in a continuous or batch process. In a preferred mode of practice, the feed composition is added in a continuous process to more precisely control fermentation conditions in the medium. In some embodiments, the feed composition is the same composition of feed added to the first medium and added to the second medium.

As another example, a first medium at the low pH (e.g., less than 5.8 or less than 5.0) and including the engineered yeast can be cultured for a period of time. The first medium can then be added to a predetermined volume of a liquid composition free of cells in a batch or bulk step to create a second medium which has a higher pH (e.g., 5.8 or greater or 6.0 or greater), which can be used for fermentation of the engineered yeast and steviol glycoside production. It is understood that there are a variety of ways a second medium having a higher pH can be prepared starting with a first medium with a lower pH. Therefore, formation of the second medium can be by a process of "adding to," "adding into," or "mixing," using bulk or continuous addition of one or more feed components. The feed components can be in liquid or in solid form. In some cases formation of the second medium can be by a multi-step process. In other cases the formation of the first medium and the second medium has the higher pH of the second medium.

In some modes of practice, the first medium is present is a vessel, and then the pH of the medium is adjusted to provide a second medium at a higher pH, which is formed in the same vessel. In other modes of practice, the first medium is formed in a first vessel and then it is transferred to a second vessel wherein the second medium having a higher pH is formed by combining the first medium with other components or materials.

The first medium having a lower pH can be formed by adding a seed culture to a liquid composition that includes a carbohydrate(s), a nitrogen source, such as yeast nitrogen base, ammonium hydroxide, urea, ammonium sulfate, yeast extract or any combination thereof; salts, vitamins, and trace metals. In some modes of practice the first medium includes ammonium hydroxide, urea, ammonium sulfate, or combinations thereof, as the sole nitrogen source in the medium. An "initial" concentration of components in the first medium may be described, with an understanding that the concentration of components may decrease in the first medium over time as the engineered cells consume the components. When the second medium with the higher pH (e.g., 5.8 or greater, or 6.0 or greater) is formed, the ammonium hydroxide, urea, or ammonium sulfate can be the sole nitrogen source in the medium.

In some modes of practice, the first medium, such as the medium where yeast growth takes place, can have a pH less than about 6.0, less than about 5.9, less than about 5.8, less than about 5.7, less than about 5.6, less than about 5.5, less than about 5.4, less than about 5.3, less than about 5.2, less than about 5.1, less than about 5.0, such as in the range of about 3.0 to about 5.5, about 3.5 to about 5.3, or about 4.0 to about 5.0. An exemplary pH in the first medium is about 5.0. During the period of growth in the first medium, the pH may fluctuate. For example, growth of the yeast cells may cause the first medium to become more acidic after a period of time. Optionally, the pH in the first medium can be controlled by monitoring the pH over time, and, if necessary, adjusting the pH such as with a base or a buffer so it remains within a desired range during growth in the first medium. For example, the pH of the first medium can be controlled using a nitrogen-containing base, such as ammonium hydroxide so the pH is maintained in the range of about 4.8 to about 5.2. A nitrogen-containing base used in the first medium can be the same as a nitrogen-containing base used in the second medium (e.g., ammonium hydroxide), with a difference being that the base used in the second medium is at a higher concentration to provide a higher pH.

In some modes of practice, the first medium can have an initial concentration of glucose that is less than about 50 g/L, less than 25 g/L, such as in the range of about 5 g/L to about 50 g/L, or about 10 g/L to about 35 g/L. The glucose concentration in the first medium may also be defined relative to the glucose concentration in the second medium.

In exemplary modes of practice, growth in the first medium is performed at a temperature in the range of about 25-35° C., or 28-32° C., and most preferably at about 30° C.

Also, growth of the engineered yeast can be performed with aeration, and with agitation.

For example, in the first medium and during the growth phase, aeration can be performed. Aeration may be described in terms of dissolved oxygen transfer rate to the medium in units of mg $min^{-1}$ $liter^{-1}$. (For example, see Anderlei, T., and Btichs, J. (2000) Biochem. Engin. J. 3478:1-6). A sparging technique that promotes the formation of fine gas bubbles can be performed to provide desired aeration. In some modes of practice, during the growth phase in the first medium, agitation and aeration is increased, such as in a stepwise manner. Aeration conditions can have an effect on the amount of oxygen dissolved in the medium, and therefore the oxygen available to the engineered yeast. The amount of oxygen uptake by the engineered yeast can be controlled by the rate at which oxygen is supplied and the formation of small oxygen bubbles in the medium, which can be achieved through agitation and/or sparging. Limited aeration can also be performed during the fermentation phase.

Growth of the engineered yeast in the first medium can be carried out for a desired period of time before adjusting to the second medium at the higher pH. In some modes of practice, growth of the engineered yeast in the first medium can be carried out for a desired period of time before adjusting to the second medium, where the first medium and second medium have the higher pH. For example, growth in the first medium can be carried out for a time of about two hours or greater, or about 10 hours or greater, such as a period of time in the range of about two hours to about 30 hours, or about 10 hours to about 24 hours. The time in the first medium may encompass all or part of the lag phase of growth, and all or part of the log (exponential) phase of growth of the engineered yeast. Further, during the time in the first medium at the lower pH, the engineered yeast can have a predetermined growth rate. For example, in the first medium the engineered yeast can have a doubling time in the range of about 2.31 hours to about 13.86 hours, or about 2.77 hours to about 7.3 hours. Alternatively, growth rate can be expressed as the dilution rate, which can be in the range of about 0.05-0.31/h, or about 0.095-0.251/h.

Growth of the engineered yeast can be performed to provide a desired amount of biomass. As used herein "biomass" refers to the weight of the engineered yeast, which can be measured in grams of dried cell weight per liter of medium (DCW/L). In some mode of practice, the engineered yeast are grown to a biomass amount of about 20 g dcw/L or greater, about 30 g dcw/L or greater, such as in the range of about 20 g dcw/L to about 120 g dcw/L, or about 40 g dcw/L to about 80 g dcw/L.

In forming the second medium, a base can be added to the first medium, which causes an increase from the lower pH to the higher pH. The time at which the base is added can be chosen based on aspects such as the time the engineered yeast have spent in the first medium, the concentration of components in the first medium at a particular time point, or the growth characteristics of the engineered yeast at a particular time point, or combinations of these aspects. In some modes of practice, the pH of the first medium is increased at a time at least halfway through the exponential (growth) phase of the engineered yeast in the first medium. For example, the pH of the first medium can be increased to about 5.8 or greater, or to about 6.0 or greater as the engineered yeast are coming out of the exponential phase, and their growth is slowing. Therefore, addition of base to raise the pH can be performed prior to the engineered yeast entering the fermentation phase with lower growth rates. Therefore, the pH of the medium can be increased following any significant production of steviol glycoside(s) from the engineered yeast in a fermentation period. However, the high pH conditions preferably encompass a period of fermentation that provides production of steviol glycoside(s) from the engineered yeast. Alternatively, addition of base to raise the pH can be performed after the engineered yeast enter the fermentation phase.

The base can be a nitrogen-containing base, such as ammonium hydroxide, or a non-nitrogen base suitable for use in a fermentation medium. A composition that includes a mixture of a nitrogen-containing base and a non-nitrogen-containing base can optionally be used. Other optional nitrogen-containing bases that can be used in the second medium can be anhydrous ammonia or an ammonium hydroxide/potassium hydroxide blend. Other optional non-nitrogen-containing bases that can be used in the second medium can be potassium hydroxide, sodium hydroxide, and calcium hydroxide. A composition that includes a nitrogen containing base in concentrated form (e.g., ammonium hydroxide up to about 15% (w/v) or greater) can be used to change the pH.

The base can be added to the first composition as a liquid composition, or can be added as a solid, for formation of the second medium. The base can be added to the first composition in a bulk method or a continuous process. In some modes of practice, the base is added in a continuous process to achieve a desired pH over a desired period of time. For example the change from the first pH to the second pH can be carried out over a short period of time (minutes), or longer times (hours), or any time in between. For example, the change can occur for a period of time in the range of about two minutes to about four hours, about five minutes to about four hours, or about 30 minutes to about three hours. In an exemplary mode of practice, a change from about pH 5.0 to about pH 7.0 can occur in a period of time in the range of about 30 minutes to about 180 minutes.

Formation of the second medium can also include providing a feed medium to the first medium. In some modes of practice, a base is added to the first medium to increase the pH from a lower to a higher pH, and then a feed composition is added to the medium at the higher pH. In other modes of practice, the feed medium includes a base and has a higher pH, and then when the feed medium is added to the first medium it increases the pH to provide the second medium.

The feed medium, with or without base, can be the same or different than the first medium in which the engineered yeast are grown. In some embodiments, the feed medium added to the first medium is the same as the feed medium added to the second medium.

The feed medium can include a carbohydrate(s), a nitrogen source, such as yeast extract, ammonium hydroxide, urea, ammonium sulfate, or any combination thereof; salts, vitamins, and trace metals such. The concentration of the components in the feed medium can be greater than the concentration of components in the first medium so that when the feed medium is added it provides desired amounts of components in the second medium suitable for fermentation of the engineered yeast. In exemplary embodiments, the concentration of glucose in the feed mediumor during fermentation (e.g. second medium) is kept in the range of about 0 g/L to about 5 g/L, or 0 g/L to about 2 g/L. In exemplary embodiments, the concentration of a nitrogen source (total amount) in the feed medium such as yeast extract, nitrogen base, ammonium hydroxide, urea, ammonium sulfate, is kept in the range of about 5 g/L to about 40 g/L. In exemplary embodiments, the concentration of salts (total amount) in the feed medium such as salts including magnesium sulfate in the range of about 0 g/L to about 12 g/L, and potassium phosphate in the range of about 0 g/L to about 22 g/L. In exemplary embodiments, the concentration of trace metals (total amount) in the feed medium is kept in the range of about 0 g/L to about 0.4 g/L, or 0 g/L to about 0.2 g/L.

During the period the engineered yeast are in the second medium, such as during a period of fermentation, the pH may fluctuate. However, the pH is preferably kept at about pH 5.8 or greater, or about pH 6.0 or greater, such as in the range of about pH 5.8 to about pH 8.0, pH 5.8 to about pH 7.5 or greater, about pH 6.0 to about pH 7.0, about 5.8 to about 6.5 or about 5.8 to about 6.2. During the period in the second medium, the pH can be monitored (e.g., periodically or continuously) and adjustments to the second medium can be made if the pH falls outside a desired range. For example, additional ammonium hydroxide can be added to the second medium if the pH drops below 5.8, so as to adjust the pH to about 5.8 or greater. In exemplary embodiments, approximately 0.17 kg to about 0.2 kg of 12% NH4OH is added during fermentation to maintain the pH at 5.0 and approximately 0.20 kg to about 0.24 kg of 12% NH4OH is added during fermentation to maintain the pH at 6.0. Approximately 1.18 kg to about 1.21 kg of feed medium is added during the feeding phase in a typical fermentation.

In exemplary embodiments, the glucose concentration was kept limiting by controlling flow rates of feed medium. A two-phase feeding strategy can include an initial exponential phase beginning at 10 hours with a growth rate for example of u=0.12 l/h while second feeding (or feed phase II) can start at 33 hours with a constant flow rate for example of 0.180 mls/minute. Feeding can continue until a final volume of about 1.95 liters can be obtained by about 120 hours. Other methods of feeding rates for producing the desired steviol glycosides are described in the application titled "Fermentation Methods for Producing Steviol Glycosides with Multi-phase Feeding," U.S. Pat. App. No. 62/168,372, and International PCT application Ser. No. PCT/US2016/034826, titled "Fermentation Methods for Producing Steviol Glycosides with Multi-phase Feeding, and filed concurrently with the present application, each application which are hereby incorporated by reference in their entirety.

The period of time the engineered yeast are present in the second medium can include a fermentation period carried out for an amount of time sufficient to produce a desired amount of steviol glycosides. For example, the second medium with higher pH can be formed at a time of 2 hours or later, 10 hours or later, or 24 hours or later, from an initial culturing of the engineered yeast, and can extend to up to a time of 150 hours, up to 96 hours, or up to 72 hours, from the initial culturing of the engineered yeast. Fermentation of the engineered yeast and production of the steviol glycoside(s) can begin at a point during residence of the engineered yeast in the second medium. Preferably most of the steviol glycoside (i.e., greater than 50%) is produced by the engineered yeast while in the in the second medium at the higher pH.

In exemplary modes of practice, fermentation and optionally growth in the second medium is performed at a temperature in the range of about 25-35° C., or 28-32° C., and most preferably at about 30° C. Also, fermentation and optionally growth of the engineered yeast in the second medium can be performed with aeration, and with agitation.

Optionally, the pH in the second medium can be controlled by monitoring the pH over time, and, if necessary, adjusting the pH in the second medium such as with a base or a buffer so it remains within a desired range during fermentation. For example, the pH of the second medium can also be controlled using a nitrogen-containing base, such as ammonium hydroxide so the pH is maintained in at about 5.8 or greater, such as in the range of about pH 5.8 to about pH 7.5 or greater, about pH 6.0 to about pH 7.0, about 5.8 to about 6.5 or 5.8 to about 6.2. A nitrogen-containing base used in the second medium can be the same as the nitrogen-containing base used in the first medium (e.g., ammonium hydroxide).

The engineered yeast can be maintained in the second medium for a period of time sufficient to produce one or more steviol glycosides. For example, the engineered yeast can be present in the second medium for a period up to about 150 hours which can include growth and fermentation phases of the process. Exemplary periods in the second medium are in the range of about 20 hours to about 150 hours, about 30 hours to about 120 hours, or about 40 hours to about 90 hours. The period in the second medium can be most of the growth phase and all of the fermentation phase, a part of the growth phase and all of the fermentation phase, all of the fermentation phase, or most of the fermentation phase.

In another embodiment, the disclosure provides a method for producing a steviol glycoside using engineered yeast in which a higher pH condition is present at an early point in the process, such as at the outset of the growth phase. For example, both the growth and fermentation phases of the process can be in a medium having a pH of 5.8 or greater, about pH 6.0 or greater, such as in the range of about pH 5.8 to about pH 8.0, pH 5.8 to about pH 7.5 greater, about pH 6.0 to about pH 7.0, about 5.8 to about 6.5 or about 5.8 to about 6.2. The medium can include a nitrogen source selected from ammonium hydroxide, urea, and ammonium sulfate. One or a combination of these compounds can be the primary nitrogen source during the growth and fermenting stages of the process.

In a process that starts with a high pH, during the periods the engineered yeast are growing and fermenting, the pH may fluctuate. However, the pH is preferably kept at about pH 5.8 or greater, or about pH 6.0 or greater, such as in the range of about pH 5.8 to about 8.0, pH 5.8 to about pH 7.5 or greater, or about pH 6.0 to about pH 7.0 during the growth and fermentation period. During these periods, the pH can be monitored (e.g., periodically or continuously) and adjustments to the medium can be made if the pH falls outside a desired range. For example, additional ammonium hydroxide can be added to the medium if the pH drops below 5.8 or 6.0, so as to adjust the pH to about 5.8 or greater.

In some modes of practice wherein the engineered yeast are present in a higher pH medium at the outset or early into the growth phase, the engineered yeast can be maintained in the medium for a period of time sufficient to produce one or more steviol glycosides. For example, the engineered yeast can be present in the higher pH medium for a period of about 150 hours, or even greater. Exemplary periods in the second medium are in the range of about 40 hours to about 150 hours, about 50 hours to about 130 hours, or about 60 hours to about 110 hours.

During fermentation, the medium at the higher pH can be monitored for the production of steviol glycosides. Fermentation can be stopped at a point where there is a desired steviol glycoside total amount and profile.

The "total steviol glycosides" (TSG) refers all the steviol glycosides present in the medium after a period of fermentation, which includes the amount of steviol glycosides in the liquid medium and obtainable from the engineered yeast. The steviol glycoside content can be expressed with regards to a total steviol glycosides amount in the medium, or the amount of one or more, but not all, steviol glycosides, in the medium. The amounts of steviol glycosides in the composition can be expressed in relation to one another, or to the total amount of steviol glycosides, such as by a weight percentage of the total amount of steviol glycosides, or a ratio, or range of ratios, expressed as weight percent, or molar percent. The sum of the content of all steviol glycosides in a composition it typically carried out on a dry (anhydrous) basis.

The amount of steviol glycosides can also be expressed relative to a control sample, such as a control sample fermented at a lower pH. An exemplary comparison is engineered yeast grown at a pH of about 5.0, and then adjusted to a pH in the range of 5.8 to 7.5 for fermentation, compared to engineered yeast grown and fermented at a pH of about 5.0, without adjusting to a higher pH. Another exemplary comparison is engineered yeast grown and fermented at pH in the range of 5.8 to 7.5 for fermentation, compared to engineered yeast grown and fermented at a pH of about 5.0.

For example, engineered yeast that are fermented at the higher pH condition, or both grown and fermented at the higher pH condition, can exhibit an increase in total steviol glycoside amount of about 1.2× or greater, about 1.3× or greater, about 1.4× or greater, about 1.5× or greater, about 1.6× or greater, about 1.7× or greater, about 1.8× or greater, about 1.9× or greater, or about 2.0× or greater, relative to the engineered yeast strain that is grown at a lower pH condition (e.g., pH 5.0).

The production of certain steviol glycosides, such as rebaudioside D and rebaudioside M, at higher pH conditions can also be described relative to engineered yeast grown at a lower pH condition. For example, engineered yeast that are fermented at the higher pH condition, or both grown and fermented at the higher pH condition, can exhibit an increase in rebaudioside D amount of about 1.4× or greater, about 1.5× or greater, about 1.6× or greater, about 1.7× or greater, about 1.8× or greater, about 1.9× or greater, about 2.0× or greater, about 2.1× or greater, relative to the engineered yeast strain that is grown at a lower pH condition (e.g., pH 5.0). Exemplary titers of rebaudioside D in the fermentation medium are about 1 g/L or greater, about 1.25 g/L or greater, about 1.5 g/L or greater, about 1.75 g/L or greater, or about 2.0 g/L or greater.

As another example, engineered yeast that are fermented at the higher pH condition, or both grown and fermented at the higher pH condition, can exhibit an increase in rebaudioside M amount of about 1.1× or greater, about 1.2× or greater, about 1.3× or greater, about 1.4× or greater, about 1.5× or greater, or about 1.6× or greater, relative to the engineered yeast strain that is grown at a lower pH condition (e.g., pH 5.0).

Engineered yeast fermented at the high pH conditions may also exhibit a change in the relative amounts of steviol glycosides produced. For example, at a lower pH, the engineered yeast may exhibit production of first and second steviol glycosides at a certain ratio (e.g., X:Y). Upon change to a higher pH fermentation condition, the engineered yeast may not only be able to produce a greater amount of the glycosides, including first and second glycosides, but may also able to produce the first and second glycosides at a ratio that is different than their production at the lower pH. In some modes of practice, the first steviol glycoside has a lower molecular weight than the second steviol glycoside. For example, with reference to rebaudioside D and rebaudioside M, fermentation at a higher pH (e.g., in the range of 5.8 to 7.5) can increase the reb D:reb M ratio as compared to the reb D reb M ratio grown at a lower pH (e.g., pH 5.0).

In some modes of practice, the method provides a fermentation composition wherein the ratio of rebaudioside D to rebaudioside M in step (b) is about 1:20 or greater, such as in the range of about 1:20 to about 1:1, about 1:5 to about 1:1, about 1:2 to about 1:1, about 1:1.75 to about 1:1, or about 1:1.5 to about 1:1. For example, engineered yeast that are fermented at the higher pH condition, or both grown and fermented at the higher pH condition, can exhibit ratios of rebaudioside D to rebaudioside M as about 1:20 or greater, such as in the range of about 1:20 to about 1:1, about 1:10 to about 1:1, about 1:7.5 to about 1:1, about 1:5 to about 1:1, about 1:3 to about 1:1, about 1:2 to about 1:1, about 1:1.75 to about 1:1, or about 1:1.5 to about 1:1.

For example, engineered yeast that are fermented at the higher pH condition, or both grown and fermented at the higher pH condition, can exhibit an increase in the reb D:reb M ratio of about 10% or greater, about 20% or greater, about 30% or greater, or about 40% or greater, relative to the reb D:reb M ratio when the engineered yeast strain are grown at a lower pH condition (e.g., pH 5.8 or less, or pH 5.0 or less).

Following the period of fermentation at the higher pH, a composition containing one or more steviol glycoside(s) can be obtained from the medium using various techniques. In some embodiments, a compound such as permeabilizing agent can be added to the medium to enhance removal of the steviol glycosides from the cell and into the medium.

The medium can then be centrifuged or filtered to remove the engineered cells. The medium can optionally be treated to remove low molecular weight components (glucose, basic nutrients, and salts), such as by membrane dialysis. Depending on a desired use, a composition comprising one or more steviol glycoside compound(s) can be used.

After fermentation the engineered yeast can optionally be treated using a heat treatment method to enhance the recovery of steviol glycosides. After fermentation, but before any heat treatment, the medium may contain a suboptimal amount of the steviol glycosides, with a portion of the desired steviol glycosides within the engineered yeast. To increase the recovery of steviol glycosides, in some modes of practice a composition, such as the medium at the higher pH in which the engineered yeast have been fermented, is heated to a temperature in the range from 50° C. to 95° C., or 70° C. to 95° C., for a period of time in the range of 5 minutes to 48 hours.

If it is desired to provide a composition with steviol glycosides in enriched or purified form, or where certain steviol glycosides are separated from one another, further purification can be carried out. Such enrichment or purification of steviol glycoside components can be carried out on the medium in which fermentation took place, or the medium can then be dried down prior to purification. For example, medium can be dried down using lyophilization to form a dry composition (e.g., powder or flakes) including steviol glycosides that can be subsequently processed.

In some modes of practice, dried fermentation broth enriched for steviol glycosides is used as the starting material for purification. For example, a solvent or solvent combination can be added to the dried fermentation broth to dissolve or suspend material that includes the steviol glycosides. An exemplary combination for dissolving the steviol glycosides is a mixture of water and an alcohol (e.g., 50:50 ethanol:water). To facilitate dissolving or suspending, the dried broth materials can be heated at a temperature above room temperature, such as in the range of 40° C.-60° C. Mechanical disruption of the dried broth materials can also be performed, such as by sonication. The dissolved or suspended broth materials can be filtered using a micron or sub-micron prior to further purification, such as by preparative chromatography.

Dried fermentation broth enriched for steviol glycoside compounds can be subjected to purification, such as by reverse phase liquid chromatography. A suitable resin can be used to retain steviol glycoside compounds in the column, with removal of hydrophilic compounds which get washed through the column with a liquid such as water. Elution of steviol glycosides from the column can be accomplished a suitable solvent or solvent combination such as acetonitrile or methanol.

Elution of steviol glycosides from a reverse phase column can yield a composition which can be useful for any one of a variety of purposes. For example, a purified steviol glycoside composition can be used as a sweetener composition for oral ingestion or oral use. The composition can be defined with regards to the steviol glycosides in the composition.

Steviol glycoside-producing *S. cerevisiae* strains were constructed using methods as described in WO 2011/153378, WO 2013/022989, WO 2014/122227, and WO 2014/122328, each of which is incorporated by reference in their entirety. The following sequences were used for construction of a parent strain (Strain A): a recombinant gene encoding a *Synechococcus* sp GGPPS polypeptide (SEQ ID NO:6), a recombinant gene encoding a truncated *Zea mays* CDPS polypeptide (SEQ ID NO:7), a recombinant gene encoding an *Arabidopsis thaliana* KS polypeptide (SEQ ID NO:8), a recombinant gene encoding a recombinant *Stevia rebaudiana* KO polypeptide (SEQ ID NO:9, SEQ ID NO:10), a recombinant gene encoding an *A. thaliana* ATR2 polypeptide (SEQ ID NO:11, SEQ ID NO:12), a recombinant gene encoding an *Oryza sativa* EUGT 11 polypeptide (SEQ ID NO:13), a recombinant gene encoding an SrKAHe1 polypeptide (SEQ ID NO:14, SEQ ID NO:15), a recombinant gene encoding an *Stevia rebaudiana* CPR8 polypeptide (SEQ ID NO:16, SEQ ID NO:17), a recombinant gene encoding an *Stevia rebaudiana* UGT85C2 polypeptide (SEQ ID NO:2), a recombinant gene encoding an *Stevia rebaudiana* UGT74G1 polypeptide (SEQ ID NO:1), a recombinant gene encoding an *Stevia rebaudiana* UGT76G1 polypeptide (SEQ ID NO:3), and a recombinant gene encoding an *Stevia rebaudiana* UGT91D2 variant (or functional homolog), UGT91D2e-b, (SEQ ID NO:4) polypeptide produced steviol glycosides.

The UGT91D2e-b variant of UGT91D2 (SEQ ID NO:5 from PCT/US2012/050021) includes a substitution of a methionine for leucine at position 211 and a substitution of an alanine for valine at position 286. (Additional variants, except T144S, M152L, L213F, S364P, and G384C variants, described in Table 12 and Example 11 of PCT/US2012/050021 could be used.) GeneArt codon-optimized sequence encoding a *Stevia rebaudiana* UGT91D2e-b with the amino acid modifications L211M and V286A (SEQ ID NO:4 for amino acid sequence; codon optimized nucleotide sequence is set forth in SEQ ID NO:5).

Strain B is derived from the parent strain described above and additionally includes a codon-optimized CPR1 from *Stevia rebaudiana* (SEQ ID NO:18 corresponding to amino acid SEQ ID NO:19).

Strain C is derived from strain B and additionally includes a gene encoding a KO polypeptide according to SEQ ID NO: 20.

Strain D is derived from strain C and additionally includes a gene encoding a KAH polypeptide according to SEQ ID NO: 21.

Strain E is derived from strain C and additionally includes a gene encoding a CPR4497 polypeptide according to SEQ ID NO: 22

Some additional non-limiting embodiments are provided below to further exemplify the present disclosure:

1. A method for producing steviol glycoside, the method comprising steps of:

(a) growing engineered yeast in a first medium at a first pH, wherein the engineered yeast are capable of producing one or more steviol glycoside(s);

(b) adding a composition to the first medium to provide a second medium with a second pH that is greater than the first pH; and (c) fermenting the engineered yeast to produce the one or more steviol glycoside(s) in the second medium at the second pH.

2. The method of embodiment 1 wherein the first pH is less than 6.0.

3. The method of embodiment 2 wherein the first pH is in the range of 4.0 to 5.5.

4. The method of embodiment 1 wherein the second pH is greater than 5.0.

5. The method of embodiment 4 wherein the second pH is in the range of 5.5 to 8.

6. The method of embodiment 5 wherein the second pH is in the range of 5.8 to 7.5.

7. The method of embodiment 1 wherein the composition comprises a nitrogen-containing compound selected from the group consisting of ammonium hydroxide, urea, and ammonium sulfate.

8. The method of embodiment 7 wherein ammonium hydroxide, urea, or ammonium sulfate is the primary nitrogen source for fermentation of the engineered yeast in the medium.

9. The method of embodiment 8 wherein ammonium hydroxide or urea is 90% (wt) or greater, or 95% (wt) or greater, of the nitrogen source for fermentation of the engineered yeast in the second medium.

10. The method of embodiment 1, where, in step (b), the composition comprises a non-nitrogen base.

11. The method of embodiment 10, wherein the non-nitrogen base is selected from the group consisting of potassium hydroxide, sodium hydroxide, and calcium hydroxide.

12. The method of embodiment 8, wherein ammonium hydroxide, urea, or ammonium sulfate is 90% (wt) or greater, or 95% (wt) or greater, of the nitrogen source for fermentation of the engineered yeast in the second medium.

13. The method of embodiment 7 where, in step (a), the first medium comprises ammonium hydroxide, urea, ammonium sulfate, or any combination thereof, and, in step (b), the second pH is achieved by adding the composition comprising ammonium hydroxide, urea, ammonium sulfate, or any combination thereof, and optionally a non-nitrogen base, to the first medium.

14. The method of embodiment 1 where the first medium comprises glucose at a concentration of not greater than 25 g/L.

15. The method of embodiment 1 where the first medium comprises glucose, a nitrogen source other than ammonium hydroxide or urea, a potassium source, a magnesium source, trace metals, and vitamins.

16. The method of embodiment 1 where, in step (b), the second medium comprises glucose at a concentration in the range of 400 g/L to 750 g/L.

17. The method of embodiment 1 where, in step (b), the second medium comprises glucose, a nitrogen source, a potassium source, a magnesium source, a phosphate source, a magnesium source, trace metals, vitamins, and an antifoam agent.

18. The method of embodiment 1 where step (b) comprises continuous or batch addition of additional fermentation material to the second medium comprising the engineered yeast.

19. The method of embodiment 1 where step (b) is performed at a time of 2 hours or later from an initial culturing of the engineered yeast.

20. The method of embodiment 1 where step (b) is performed up to a time of 150 hours from an initial culturing of the engineered yeast.

21. The method of embodiment 20 where step (b) is performed at a time of 10 hours or later, and up to 96 hours, from an initial culturing of the engineered yeast.

22. The method of embodiment 21 where step (b) is performed at a time of 24 hours or later, and up to 72 hours, from an initial culturing of the engineered yeast.

23. The method of embodiment 1 wherein the engineered yeast produce an amount of the one or more steviol glycoside(s) in step (b) at the second pH that is 10% or greater than an amount of the one or more steviol glycoside(s) produced when engineered yeast are maintained at the first pH throughout fermentation.

24. The method of embodiment 23 wherein the engineered yeast produce an amount of the one or more steviol glycoside(s) in step (b) at the second pH that is 20% or greater than an amount of the one or more steviol glycoside(s) produced when engineered yeast are maintained at the first pH throughout fermentation.

25. The method of embodiment 1 wherein the one or more steviol glycoside(s) comprise rebaudioside M, rebaudioside D, or both rebaudioside M and rebaudioside D.

26. The method of embodiment 25 wherein the engineered yeast produce a ratio of rebaudioside D to rebaudioside M in step (b) at the second pH that is greater than a ratio of rebaudioside D to rebaudioside M produced when engineered yeast are maintained at the first pH throughout fermentation.

27. The method of embodiment 26 wherein the ratio of rebaudioside D to rebaudioside M in step (b) is 1:20 or greater.

28. The method of embodiment 27 wherein the ratio of rebaudioside D to rebaudioside M in step (b) is in the range of 1:20 to 1:1.

29. The method of embodiment 1 wherein the engineered yeast is selected from the group consisting of species of *Candida*, *Kloeckera* (*Hanseniaspora*), *Kluyveromyces*, *Lipomyces*, *Pichia* (*Hansenula*), *Rhodotorula*, *Saccharomycete*, *Saccharomyces*, *Schizosaccharomyces*, *Torulopsis*, *Torulaspora*, *Yarrowia*, and *Zygosaccharomyces*.

30. The method of embodiment 29 wherein the engineered yeast is *Saccharomyces cerevisiae*.

31. The method of embodiment 1 wherein the engineered yeast expresses one or more exogenous nucleic acid(s) encoding one or more of the following proteins heterologous to the yeast: GGPPS polypeptide, an enf-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91 d2 polypeptide, and a EUGT11 polypeptide 32. The method of embodiment 1 wherein the engineered yeast expresses one or more exogenous nucleic acid(s) encoding one or more of the following proteins heterologous to the yeast: a GGPPS polypeptide, a truncated *Zea mays* CDPS polypeptide, an *A. thaliana* KS polypeptide a *S. rebaudiana* KO polypeptide, an *A. thaliana* ATR2 polypeptide, an *O. sativa* EUGT 11 polypeptide, a SrKAHe1 polypeptide, a *S. rebaudiana* CPR8 polypeptide, an *S. rebaudiana* UGT85C2 polypeptide, an *S. rebaudiana* UGT74G1 polypeptide, a *S. rebaudiana* UGT76G1 polypeptide, a *S. rebaudiana* UGT91D2 variant or functional homolog, and a UGT91D2e-b polypeptide.

33. The method of any of the previous embodiments further comprising a step of providing a seed medium comprising the engineered yeast, wherein the seed medium is subsequently used to form the first medium at the first pH.

34. The method of any of the previous embodiments wherein steps (a)-(c) are performed in a single vessel.

35. The method of any one of embodiments 1-33 wherein steps (a)-(c) are performed in a two or more different vessels.

36. A method for producing steviol glycoside, the method comprising a step of: fermenting an engineered yeast at a pH of 6.0 or greater in a fermentation medium, wherein the engineered yeast to produce one or more steviol glycoside(s).

37. The method of embodiment 36 wherein the fermentation medium comprises a nitrogen source selected from ammonium hydroxide, urea, and ammonium sulfate.

38. The method of embodiment 37 wherein the pH is in the range of 6.0 to 7.5.

39. The method of embodiment 38 wherein the pH is in the range of 6.5 to 7.5.

40. The method of embodiment 36 wherein ammonium hydroxide or urea is 90% (wt) or greater, or 95% (wt) or greater, of the nitrogen source for fermentation of the engineered yeast in the medium.

41. The method of embodiment 36 where the medium comprises glucose, a nitrogen source, a potassium source, a magnesium source, a phosphate source, a magnesium source, trace metals, vitamins, and an antifoam agent.

42. The method of embodiment 36 further comprising continuous or batch addition of additional fermentation material to the medium comprising the engineered yeast.

43. The method of embodiment 36 performed for a period of time of up to 150 hours.

44. The method of embodiment 43 performed for a period of time in the range of 8 to 88 hours.

45. The method of embodiment 44 performed for a period of time in the range of 22 to 48 hours.

46. The method of embodiment 36 wherein the one or more steviol glycoside(s) comprise rebaudioside M, rebaudioside D, or both rebaudioside M and rebaudioside D.

47. The method of embodiment 33 wherein the fermentation media has a biomass in the range of 20-120 g dcw/L.

48. A method for increasing the production of a first, lower molecular weight steviol glycoside relative to a second, higher molecular weight steviol glycoside in an engineered yeast, the method comprising a step of fermenting engineered yeast capable of producing one or more steviol glycoside(s) at a pH of 6.0 or greater in a fermentation medium, wherein the engineered yeast to produce a ratio of the first and second steviol glycosides at pH of 6.0 or greater that is greater than a ratio of the first and second steviol glycosides produced at a pH that is less than 6.0.

49. The method of embodiment 48 wherein the ratio of the first and second steviol glycosides at pH of 6.0 or greater is 10% or greater than the ratio of the first and second steviol glycosides produced at a pH that is less than 6.0.

50. The method of embodiment 49 wherein the ratio of the first and second steviol glycosides at pH of 6.0 or greater is 25% or greater than the ratio of the first and second steviol glycosides produced at a pH that is less than 6.0.

51. The method of embodiment 48 wherein the first steviol glycoside is rebaudioside D and the second steviol glycoside is rebaudioside M.

52. A composition derived from a fermentation method which uses engineered yeast to produce the one or more steviol glycoside(s), the composition comprising rebaudioside D and rebaudioside M at a ratio of 1:20 or greater, respectively.

53. The composition of embodiment 52 comprising rebaudioside D and rebaudioside M at a ratio in the range of 1:5 to 1:1, respectively.

54. The composition of embodiment 53 comprising rebaudioside D and rebaudioside M at a ratio in the range of 1:1.75 to 1:1, respectively.

55. The composition of embodiment 54 comprising rebaudioside D and rebaudioside Mat a ratio in the range of 1:1.5 to 1:1, respectively.

56. The composition of any one of embodiments 52-55 which is a fermentation medium.

57. The composition of embodiment 56 wherein the fermentation medium has a rebaudioside D concentration of 1 g/L or greater, 1.25 g/L or greater, 1.5 g/L or greater, 1.75 g/L or greater, or 2.0 g/L or greater.

Example 1

Production of Reb D and Reb M in Fed Batch Fermentation at Higher pH with Urea or Ammonium Hydroxide as the Primary N Source For inoculum preparation, the yeast strains B and strains C were cultured in 150 mLs of seed flask medium in 1 liter shake flasks at 250 rpm and 30° C. for 20-24 hours.

TABLE 1

Seed Flask Medium

| Component | Formula | Concentration | Units |
| --- | --- | --- | --- |
| Biospringer 0251 yeast extract | | 7.5 | g/L |
| Glucose monohydrate | $C_6H_{12}O_6$* $H_2O$ | 22.0 | g/L |

For the fermentation, 75 mLs of seed culture was transferred into initial fermentation medium (Tables 2, 3 and 4) with a starting volume of 0.75 liters. Fermentation was carried out in 2 L New Brunswick BioFlo 310 fermentors. Temperature was maintained at 30° C. throughout. The air flow rate was maintained such that the dissolved oxygen was less than 20%, and the agitation rate was automatically controlled to increase in a stepwise manner from 400 to 900 rpm during the fermentation. Glucose concentration was kept limiting by controlling flow rates of feed medium (Table 5). A 2-phase feeding strategy involved an initial exponential phase beginning at 10 hours with a growth rate of u=0.12 l/h while the 2nd phase of feeding (or feed phase II) started at 33 hours with a constant flow rate of 0.180 mls/minute. Feeding was continued until a final volume of 1.95 liters was obtained by 120 hours.

In one set of treatments with strain B, pH was controlled at pH 5 with 12% NH4OH. Then in the 2nd feeding phase, pH was either controlled at 5 or ramped up to pH 6 or pH 7 with NH4OH. Antifoam addition was controlled by utilization of foam control probes with 10 wt % antifoam solution (Ivanhoe 1163B). See results in Table 6.

Results for strain C with pH control at pH 5 with 12% NH4OH are shown in Table 7.

In another set of treatments with strain B, fermentation was controlled at 1) pH 5.0 with 12% NH4OH or 2) with only 6.2N KOH (pH drifted up to 7) with urea present in the feed. Results are shown in Table 8.

The medium was based on Verduyn et al (Verduyn C, Postma E, Scheffers W A, Van Dijken J P. Yeast. 1992 July; 8(7):501-17) with modifications as described in Tables 2 through 5. For the urea treatments, ammonium sulfate was increased to 15 g/L in the initial fermentation medium and urea was added to 39 g/L in the fermentation feed medium. KOH was used as the base for pH control in the urea treatments instead of NH4OH.

TABLE 2

Initial Fermentation Medium

| Component | Formula | Concentration | Units |
| --- | --- | --- | --- |
| Glucose monohydrate | $C_6H_{12}O_6$* $H_2O$ | 22.0 | g/L |
| Ammonium sulfate | $(NH_4)_2SO_4$ | 5.0 | g/L |
| Monobasic potassium phosphate | $KH_2PO_4$ | 3.0 | g/L |
| Magnesium sulfate heptahydrate | $MgSO_4$* 7 $H_2O$ | 0.5 | g/L |
| Trace metals stock | | 10.0 | ml/L |
| Vitamin stock | | 12.0 | ml/L |

TABLE 3

Trace Metals Stock Solution

| Component | Formula | Concentration | Units |
| --- | --- | --- | --- |
| Disodium edetate | $C_{10}H_{14}N_2Na_2O_8$ * 2$H_2O$ | 15 | g/L |
| Zinc sulfate heptahydrate | $ZnSO_4$ * 7$H_2O$ | 4.5 | g/L |

TABLE 3-continued

Trace Metals Stock Solution

| Component | Formula | Concentration | Units |
|---|---|---|---|
| Manganese (II) chloride tetrahydrate | $MnCl_2 * 4H_2O$ | 1.026 | g/L |
| Cobalt (II) chloride hexahydrate | $CoCl_2 * 6H_2O$ | 0.32 | g/L |
| Copper (II) sulfate heptahydrate | $CuSO_4 * 5H_2O$ | 0.3 | g/L |
| Sodium molybdate dihydrate | $Na_2MoO_4 * 2H_2O$ | 0.4 | g/L |
| Calcium chloride dihydrate | $CaCl_2 * 2H_2O$ | 3 | g/L |
| Iron (II) sulfate heptahydrate | $FeSO_4 * 7H_2O$ | 3 | g/L |
| Boric acid | $H_3BO_3$ | 1 | g/L |
| Potassium iodide | KI | 0.1 | g/L |

TABLE 4

Vitamin Stock Solution

| Component | Formula | Concentration | Units |
|---|---|---|---|
| d-Biotin | $C_{10}H_{16}N_2O_3S$ | 50 | mg/L |
| Calcium pantothenate | $C_{18}H_{32}CaN_2O_{10}$ | 1000 | mg/L |
| Nicotinic acid | $C_6H_5NO_2$ | 1000 | mg/L |
| Thiamine hydrochloride | $C_{12}H_{17}ClN_4OS \cdot HCl$ | 1000 | mg/L |
| Pyridoxine hydrochloride | $C_8H_{11}NO_3 \cdot HCl$ | 1000 | mg/L |
| p-aminobenzoic acid | $C_7H_7NO_2$ | 200 | mg/L |
| myo-inositol | $C_6H_{12}O_6$ | 25000 | mg/L |

TABLE 5

Fermentation Feed Medium

| Component | Formula | Concentration | Units |
|---|---|---|---|
| Glucose monohydrate | $C_6H_{12}O_6 * H_2O$ | 660 | g/L |
| Urea (in urea treatments only) | $NH_2CONH_2$ | 33 | g/L |
| Antifoam | | 1.3 | g/L |
| Potassium sulfate | $K_2SO_4$ | 4.2 | g/L |
| Sodium sulfate | $Na_2SO_4$ | 0.336 | g/L |
| Magnesium sulfate heptahydrate | $MgSO_4 * 7H_2O$ | 6.12 | g/L |
| Monobasic potassium phosphate | $KH_2PO_4$ | 10.8 | g/L |
| Trace metal stock | | 14.4 | mL/L |
| Vitamin stock | | 14.4 | mL/L |

Reb DM yields on glucose were calculated based on total glucose utilized. Yield of Reb DM on biomass was based on cell dry weight. Reb DM productivity was calculated based on summing Reb D and Reb M concentrations and dividing by final fermentation time which was determined as the time the feed medium was emptied. Biomass determination of cell dry weights was based on the filtration/oven method common in the art. Quantification of steviol glycoside can be carried out by high performance liquid chromatography (HPLC) analysis as described below, and compared against calibration curves obtained using authentic standards purchased from Chromadex.

100 µL of the fermentation media were pipetted into a 2 mL microcentrifuge tube. 900 µL of 61% methanol (extraction solvent) was added into the 2 ml microcentrifuge tube and agitated by placing on a sample rotator for 10 min to extract the steviol glycosides. The samples were then centrifuged at 10K rpm in a microcentrifuge for 3 min and the clarified supernatant was pipetted into an autosampler vial for analysis.

UHPLC Method for Glycoside Separation

[The steviol glycosides were separated using two Agilent SB-C18 RRHD columns in series (2.1 mm×150 mm, 1.8 urn) with a stem filter assembly from Optimize Technologies installed as a pre-column filter. The mobile phase used was channel A: 0.01% trifluroacetic acid (TFA) in water and channel B acetonitrile. The flow rate was 0.38 mL/min, the column temperature was 65° C. and the detection was performed at ultraviolet absorption of 210 nm. The gradient elution profile is shown below:

| Time | % Channel A | % Channel B |
|---|---|---|
| 0 | 85 | 15 |
| 0.5 | 85 | 15 |
| 30 | 75 | 25 |
| 40 | 65 | 35 |
| 49 | 47 | 53 |
| 49.1 | 0 | 100 |
| 58 | 0 | 100 |
| 58.1 | 85 | 15 |
| 62 | 85 | 15 |

Calibration was performed using Reb A (98.85% purity) from Cargill, Inc lot 1008-005 in 55% MeOH at the following concentrations: 0.35, 0.175, 0.07, 0.035, 0.014, 0.007 mg/mL. All glycosides are quantitated off of the Reb A curve. Experimental correction factors for Reb D, Reb M, and Reb B were determined against Reb A while all other analytes are corrected by molecular weight. Attached is an example of a typical fermentation broth.

Tables 6a and 6b—SG production for Strain B with $NH_4OH$ and higher pH setpoints

| | % of Control (pH 5 with NH4OH) | | | | | |
|---|---|---|---|---|---|---|
| Treatment | Reb D | Reb M | Yield of Reb DM on glucose | Yield of Reb DM on biomass | Reb DM Productivity | Biomass |
| NH4OH with pH 5 throughout | 100.0 | 100.0 | 100.0 | 100.0 | 100.0 | 100.0 |
| NH4OH with pH 6 in feed phase II | 207.7 | 153.1 | 166.7 | 173.1 | 169.6 | 101.2 |
| NH4OH with pH 7 in feed phase II | 195.6 | 126.3 | 144.4 | 219.2 | 156.5 | 68.9 |

TABLE 6b

| Treatment | Reb D titer (g/L) | Reb M titer (g/L) | Reb D to Reb M ratio | % of Control (pH 5 with NH4OH) | | | |
|---|---|---|---|---|---|---|---|
| | | | | Yield of Reb DM on glucose | Yield of Reb DM on biomass | Reb DM Productivity | Biomass |
| NH4OH with pH 5 throughout | 0.91 | 1.79 | 1:1.96 | 100.0 | 100.0 | 100.0 | 100.0 |
| NH4OH with pH 6 in feed phase II | 1.89 | 2.74 | 1:1.45 | 166.7 | 173.1 | 169.6 | 101.2 |
| NH4OH with pH 7 in feed phase II | 1.78 | 2.26 | 1:1.27 | 144.4 | 219.2 | 156.5 | 68.9 |

In Tables 6a and 6b, % Reb DM yield on glucose=Reb DM in g/L/glucose consumed in g/L*100. % Reb DM yield on biomass=Reb DM in g/L/biomass produced in g cell dry weight (CDW or DCW)/L*100. Reb D and Reb M titers originally measured in in g/L. Comparison to control is the treatment value divided by the control value*100%. For example, Reb D of treatment in g/L divided by Reb D of control*100% equals % of control.

Tables 7a and 7b—SG production for Strain C with NH$_4$OH and a high pH setpoint

| Strain | Treatment | % of Control (pH 5 with NH$_4$OH) Reb DM |
|---|---|---|
| C | NH$_4$OH with pH 5 throughout | 100.0 |
| C | NH$_4$OH with pH 6 in feed phase II | 135.0 |

TABLE 7B

| Strain | pH | Reb D titer (g/L) | Reb M titer (g/L) | Reb D to Reb M ratio |
|---|---|---|---|---|
| C | pH 5 throughout | 0.74 | 4.15 | 1:5.6 |
| C | pH 6 in feed phase II | 1.51 | 5.10 | 1:3.3 |

Tables 8a and 8b—SG production for Strain B with urea and higher pH

| Treatment | | % of Control | | | | | |
|---|---|---|---|---|---|---|---|
| pH during fermentation | Primary N source | Reb D | Reb M | Yield of Reb DM on glucose | Yield of Reb DM on biomass | Reb DM productivity | Biomass |
| pH 5 throughout (control) | NH$_4$OH | 100.0 | 100.0 | 100.0 | 100.0 | 100.0 | 100.0 |
| pH 5 then drift to pH 7 in 2nd feed phase | Urea | 202.7 | 117.0 | 145.4 | 182.3 | 151.2 | 79.8 |

| Treatment | | % of Control | | | | | |
|---|---|---|---|---|---|---|---|
| pH during fermentation | Primary N source | Reb D (g/L) | Reb M (g/L) | Reb D to Reb M ratio | Yield of Reb DM on glucose | Yield of Reb DM on biomass | Reb DM productivity | Biomass |
| pH 5 throughout (control) | NH$_4$OH | 1.22 | 2.47 | 1:2.0 | 100.0 | 100.0 | 100.0 | 100.0 |
| pH 5 then drift to pH 7 in 2nd feed phase | Urea | 2.48 | 2.89 | 1:1.16 | 145.4 | 182.3 | 151.2 | 79.8 |

Fermentation of the engineered yeast at the higher pH provided increased titers, production rates and yields, and increased specific rates of steviol glycosides Reb D and Reb M. The higher pH fermentation also provided increased ratios of Reb D:Reb M. The increased titer of Reb D and Reb M was observed with multiple strains at the higher pH conditions.

Example 2

Production of Reb D and Reb M in Fed Batch Fermentation at Higher pH

Fed-batch fermentation was carried out aerobically in 2 L (working volume) fermenters. 500 mL of initial mineral medium (Table 9) was inoculated using a seed culture grown in the same medium to reach an initial OD of 0.2. The culture was run in batch mode for 18 hours and then operated in fed-batch mode during ~110 hours using a 4 phase exponential feed profile and the feed medium described in Table 2. Glucose was utilized as the carbon and energy source and its concentration was kept limiting by controlling flow rates in order to allow for a fully respiratory metabolism (minimizing ethanol formation). Air flow was kept at ~1 vvm during the whole process and stirring set to 800 rpm during the first 42 hours then increased and maintained at 1200 rpm for the rest of the process. The temperature was controlled to 30° C. throughout the fermentation.

In the default fermentation set-up, the pH was controlled at pH 5.0 using 8% NH4OH during the first 42 hours and then moving to 16% NH4OH for the rest of the process.

In one set of treatments, fermentation was initially controlled at pH 5.0 using 8% NH4OH during the first 42 hours and then ramped up to pH 6.0 in a time interval of 5 h (0.2 pH units increase per hour) until the end of the process using 16% NH4OH. See the results shown in Table 13. In a second set of treatments, the pH of the fermentation was controlled at pH 6.0 throughout the process using NH4OH during the first 42 hours and 16% NH4OH from that moment onwards. See the results shown in Table 14.

In all the sets of conditions described above, 700 mL of feed medium were employed.

Whole culture samples (without cell removal) were taken and boiled in an equal volume of DMSO for Reb D and Reb M levels as described in Example 1.

TABLE 9

Initial mineral fermentation medium

|  | Concentration |  |
| --- | --- | --- |
| $(NH_4)_2SO_4$ | 5 | g/L |
| $KH_2PO_4$ | 3 |  |
| $MgSO_4 \cdot 7 H_2O$ | 0.5 |  |
| Glucose monohydrate | 22 |  |
| Antifoam 204 | 0.8 | mL/L |
| Trace metal stock (Table 3) | 10 |  |
| Vitamin stock (Table 4) | 12 |  |

TABLE 10

Fermentation feed medium

|  | Concentration |  |
| --- | --- | --- |
| $KH_2PO_4$ | 10.8 | g/L |
| $MgSO_4 \cdot 7 H_2O$ | 6.12 |  |
| $K_2SO_4$ | 4.2 |  |
| $Na_2SO_4$ | 0.336 |  |
| Glucose monohydrate | 660 |  |
| Antifoam 204 | 1 | mL/L |
| Trace metal stock (Table 3) | 14.4 |  |
| Vitamin stock (Table 4) | 14.4 |  |

TABLE 11

Trace metal stock solution

|  | Concentration |  |
| --- | --- | --- |
| $Na_2$-EDTA | 15 | g/L |
| $ZnSO_4 \cdot 7H_2O$ | 4.5 |  |
| $MnCl_2 \cdot 2H_2O$ | 0.84 |  |
| $CoCl_2 \cdot 6H_2O$ | 0.32 |  |
| $CuSO_4 \cdot 5H_2O$ | 0.3 |  |
| $Na_2MoO4 \cdot 2H_2O$ | 0.4 |  |
| $CaCl_2$ | 2.265 |  |
| $FeSO4 \cdot 7H_2O$ | 3.0 |  |
| $H_3BO_3$ | 1.0 |  |
| KI | 0.1 |  |

TABLE 12

Vitamin stock solution

|  | Concentration |  |
| --- | --- | --- |
| d-biotin | 0.05 | g/L |
| Calcium pantothenate | 1.0 |  |
| Nicotinic acid | 1.0 |  |
| Thiamine-HCl | 1.0 |  |
| Pyridoxine-HCl | 1.0 |  |
| 4-aminobenzoic acid | 0.2 |  |
| Myo-inositol | 25.0 |  |

A summary of results for fermentations performed using yeast strain E at pH 5.0 (control) vs. high pH is shown in Table 13. Normalized results are presented for all steviol glycosides measured in the total broth sample.

TABLE 13

| Strain | pH | RebD (%) | RebM (%) | RebD (g/L) | RebM (g/L) | RebD/rebM ratio |
| --- | --- | --- | --- | --- | --- | --- |
| E | 5.0 | 100 | 100 | 0.73 | 3.1 | 0.24 |
|  | 5.0 -> 6.0 | 189 | 123 | 1.38 | 3.84 | 0.36 |

A summary of results for fermentations performed using yeast strain D at pH 5.0 (control) vs. high pH is shown in Table 14. Normalized results for all steviol glycosides measured in the total broth sample are presented in the table below.

TABLE 14

| Strain | pH | RebD (%) | RebM (%) | RebD (g/L) | RebM (g/L) | RebD/rebM ratio |
|---|---|---|---|---|---|---|
| D | 5.0 throughout | 100 | 100 | 1.61 | 2.47 | 1.54 |
|   | 6.0 throughout | 134 | 103 | 2.15 | 2.54 | 1.18 |

In this example all of the fermentation elapsed times were equivalent and the amount of substrate fed (glucose) was the same in all cases. Therefore, operating the fermentation process at pH 6.0, both from the beginning of the batch phase or performing a ramp up after the first 42 hours resulted in, increased titers of Reb D and M with additional strains, increased yields on glucose, and increased production rates.

What is claimed is:

1. A method for producing steviol glycoside, comprising:
(a) growing engineered yeast in a first medium at a first pH, wherein the engineered yeast are capable of producing one or more steviol glycoside(s);
wherein the first pH is less than 5.5;
(b) adding a composition to the first medium to provide a second medium with a second pH that is greater than the first pH;
wherein the second pH is in the range of 5.8 to 8; and
(c) fermenting the second medium with the engineered yeast to produce the one or more steviol glycoside(s) in the second medium at the second pH,
wherein the one or more steviol glycosides comprise rebaudioside D and rebaudioside M;
wherein the engineered yeast produce a ratio of rebaudioside D to rebaudioside M in step (b) at the second pH that is at least 25% greater than a ratio of rebaudioside D to rebaudioside M produced when engineered yeast are maintained at the first pH throughout fermentation.

2. The method of claim 1, wherein the first pH is in the range of 4.0 to 5.5.

3. The method of claim 1, wherein the second pH is in the range of 5.8 to 7.5.

4. The method of claim 1, wherein the second pH is in the range of 6.5 to 7.5.

5. The method of claim 1, wherein the second pH is in the range of 5.8 to 6.5.

6. The method of claim 1, wherein the second pH is in the range of 5.8 to 6.2.

7. The method of claim 1, wherein the composition comprises a nitrogen-containing compound selected from the group consisting of ammonium hydroxide, yeast extract, urea, and ammonium sulfate.

8. The method of claim 1, wherein a nitrogen source comprising 90% (wt) or greater ammonium hydroxide, ammonium sulfate, or urea is used for fermentation of the engineered yeast in the second medium.

9. The method of claim 1, wherein, in step (b), the composition comprises a non-nitrogen base selected from the group consisting of potassium hydroxide, sodium hydroxide, and calcium hydroxide.

10. The method of claim 1, wherein the first medium comprises glucose at a concentration of not greater than 25 g/L.

11. The method of claim 1 wherein, in step (b), the second medium comprises glucose at a concentration in the range of 400 g/L to 750 g/L.

12. The method of claim 1, wherein step (b) is performed at a time of 2 hours or later from an initial culturing of the engineered yeast.

13. The method of claim 1, wherein step (b) is performed at a time of 10 hours or later, and up to 96 hours, from an initial culturing of the engineered yeast.

14. The method of claim 1, wherein step (b) is performed at a time of 24 hours or later, and up to 72 hours, from an initial culturing of the engineered yeast.

15. The method of claim 1, wherein the engineered yeast produce an amount of the one or more steviol glycoside(s) in step (b) at the second pH that is 10% or greater than an amount of the one or more steviol glycoside(s) produced when engineered yeast are maintained at the first pH throughout fermentation.

16. The method of claim 1, wherein the ratio of rebaudioside D to rebaudioside M in step (b) is 1:20 or greater.

17. The method of claim 1, wherein the ratio of rebaudioside D to rebaudioside M in step (b) is in the range of 1:20 to 1:1.

18. The method of claim 1, wherein the engineered yeast is selected from the group consisting of Candida, Kloeckera (Hanseniaspora), Kluyveromyces, Lipomyces, Pichia (Hansenula), Rhodotorula, Saccharomycete, Saccharomyces, Schizosaccharomyces, Torulopsis, Torulaspora, Yarrowia, and Zygosaccharomyces.

19. The method of claim 1, wherein the engineered yeast is Saccharomyces cerevisiae.

20. The method of claim 1, wherein the engineered yeast expresses one or more exogenous nucleic acid(s) encoding one or more of the following proteins heterologous to the yeast: GGPPS polypeptide, an ent-copalyl diphosphate synthase (CDPS) polypeptide, a kaurene oxidase (KO) polypeptide, a kaurene synthase (KS) polypeptide; a steviol synthase (KAH) polypeptide, a cytochrome P450 reductase (CPR) polypeptide, a UGT74G1 polypeptide, a UGT76G1 polypeptide, a UGT91-D2 polypeptide, and a EUGT11 polypeptide.

21. The method of claim 1, wherein the engineered yeast expresses one or more exogenous nucleic acid(s) encoding one or more of the following proteins heterologous to the yeast: a GGPPS polypeptide (SEQ ID NO: 6), a truncated Zea mays CDPS polypeptide (SEQ ID NO: 7), an Arabidopsis thaliana KS polypeptide (SEQ ID NO: 8), a Stevia rebaudiana KO polypeptide (SEQ ID NO: 9), an Arabidopsis thaliana ATR2 polypeptide (SEQ ID NO: 11), an Oryza sativa EUGT 11 polypeptide (SEQ ID NO: 13), a SrKAHe1 polypeptide (SEQ ID NO: 14), a Stevia rebaudiana CPR8 polypeptide (SEQ ID NO: 16), an Stevia rebaudiana UGT85C2 (SEQ ID NO: 2), polypeptide, an Stevia rebaudiana UGT74G1 polypeptide (SEQ ID NO: 1), a Stevia rebaudiana UGT76G1 polypeptide (SEQ ID NO: 3), a Stevia rebaudiana UGT91D2 (SEQ ID NO: 4), variant or functional homolog, and a UGT91D2e-b polypeptide (SEQ ID NO:5).

* * * * *

SEQUENCE LISTING

```
<160> NUMBER OF SEQ ID NOS: 22

<210> SEQ ID NO 1
<211> LENGTH: 460
<212> TYPE: PRT
<213> ORGANISM: Stevia rebaudiana

<400> SEQUENCE: 1

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Lys Asp Asn Gly Phe Asn Leu
                245                 250                 255

Tyr Lys Ala Asn His His Glu Cys Met Asn Trp Leu Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300
```

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
            325                 330                 335

Cys Lys Gln Leu Asp Val Leu Ala His Glu Ser Val Gly Cys Phe Val
                340                 345                 350

Thr His Cys Gly Phe Asn Ser Thr Leu Glu Ala Ile Ser Leu Gly Val
            355                 360                 365

Pro Val Val Ala Met Pro Gln Phe Ser Asp Gln Thr Thr Asn Ala Lys
        370                 375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
                435                 440                 445

Asp Ile Val Glu Phe Val Ser Glu Leu Ile Lys Ala
    450                 455                 460

<210> SEQ ID NO 2
<211> LENGTH: 481
<212> TYPE: PRT
<213> ORGANISM: Stevia rebaudiana

<400> SEQUENCE: 2

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65                  70                  75                  80

Pro Glu Ala Ser Ile Pro Ile Arg Glu Ser Leu Leu Arg Ser Ile Glu
                85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
        115                 120                 125

Asp Ala Ala Lys Lys Leu Gly Ile Pro Val Met Met Tyr Trp Thr Leu
    130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
                165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
        195                 200                 205

Met Phe Thr Thr Glu Ala Pro Gln Arg Ser His Lys Val Ser His His

```
            210                 215                 220
Ile Phe His Thr Phe Asp Glu Leu Glu Pro Ser Ile Lys Thr Leu
225                 230                 235                 240

Ser Leu Arg Tyr Asn His Ile Tyr Thr Ile Gly Pro Leu Gln Leu Leu
                245                 250                 255

Leu Asp Gln Ile Pro Glu Glu Lys Lys Gln Thr Gly Ile Thr Ser Leu
                260                 265                 270

His Gly Tyr Ser Leu Val Lys Glu Pro Glu Cys Phe Gln Trp Leu
                275                 280                 285

Gln Ser Lys Glu Pro Asn Ser Val Val Tyr Val Asn Phe Gly Ser Thr
290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
                325                 330                 335

Gly Glu Asn Ala Val Leu Pro Pro Glu Leu Glu Glu His Ile Lys Lys
                340                 345                 350

Arg Gly Phe Ile Ala Ser Trp Cys Ser Gln Glu Lys Val Leu Lys His
                355                 360                 365

Pro Ser Val Gly Gly Phe Leu Thr His Cys Gly Trp Gly Ser Thr Ile
                370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly
                405                 410                 415

Leu Glu Met Gly Thr Lys Val Lys Arg Asp Glu Val Lys Arg Leu Val
                420                 425                 430

Gln Glu Leu Met Gly Glu Gly Gly His Lys Met Arg Asn Lys Ala Lys
                435                 440                 445

Asp Trp Lys Glu Lys Ala Arg Ile Ala Ile Ala Pro Asn Gly Ser Ser
                450                 455                 460

Ser Leu Asn Ile Asp Lys Met Val Lys Glu Ile Thr Val Leu Ala Arg
465                 470                 475                 480

Asn

<210> SEQ ID NO 3
<211> LENGTH: 458
<212> TYPE: PRT
<213> ORGANISM: Stevia rebaudiana

<400> SEQUENCE: 3

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
                35                  40                  45

Asn Phe Asn Lys Pro Lys Thr Ser Asn Tyr Pro His Phe Thr Phe Arg
                50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
```

```
            100                 105                 110
Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
        370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 4
<211> LENGTH: 473
<212> TYPE: PRT
<213> ORGANISM: Stevia rebaudiana

<400> SEQUENCE: 4

Met Ala Thr Ser Asp Ser Ile Val Asp Asp Arg Lys Gln Leu His Val
1               5                   10                  15
```

```
Ala Thr Phe Pro Trp Leu Ala Phe Gly His Ile Leu Pro Tyr Leu Gln
             20                  25                  30

Leu Ser Lys Leu Ile Ala Glu Lys Gly His Lys Val Ser Phe Leu Ser
         35                  40                  45

Thr Thr Arg Asn Ile Gln Arg Leu Ser Ser His Ile Ser Pro Leu Ile
     50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                 85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
        130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Met Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Ala Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
```

Glu Lys Glu Tyr Val Ser Gln Phe Val Asp Tyr Leu Glu Lys Asn Ala
            450                 455                 460

Arg Ala Val Ala Ile Asp His Glu Ser
465                 470

<210> SEQ ID NO 5
<211> LENGTH: 1422
<212> TYPE: DNA
<213> ORGANISM: Artificial Sequence
<220> FEATURE:
<223> OTHER INFORMATION: Synthetic oligonucleotide

<400> SEQUENCE: 5

```
atggctactt ctgattccat cgttgacgat agaaagcaat tgcatgttgc tactttcca      60
tggttggctt tcggtcatat tttgccatac ttgcaattgt ccaagttgat tgctgaaaag    120
ggtcacaagg tttcattctt gtctaccacc agaaacatcc aaagattgtc ctctcatatc    180
tccccattga tcaacgttgt tcaattgact ttgccaagag tccaagaatt gccagaagat    240
gctgaagcta ctactgatgt tcatccagaa gatatccctt acttgaaaaa ggcttccgat    300
ggtttacaac agaagttac tagattcttg aacaacatt ccccagattg gatcatctac      360
gattatactc attactggtt gccatccatt gctgcttcat gggtatttc tagagcccat     420
ttctctgtta ctactccatg ggctattgct tatatgggtc catctgctga tgctatgatt    480
aacggttctg atggtagaac taccgttgaa gatttgacta ctccaccaaa gtggtttcca    540
tttccaacaa aagtctgttg agaaaaacac gatttggcta gattggttcc atacaaagct    600
ccaggtattt ctgatggtta cagaatgggt atggttttga aggttccga ttgcttgttg     660
tctaagtgct atcatgaatt cggtactcaa tggttgcctt tgttggaaac attgcatcaa    720
gttccagttg ttccagtagg tttgttgcca ccagaaattc caggtgacga aaaagacgaa    780
acttgggttt ccatcaaaaa gtggttggat ggtaagcaaa agggttctgt tgtttatgtt    840
gctttgggtt ccgaagcttt ggtttctcaa accgaagttg ttgaattggc tttgggtttg    900
gaattgtctg gtttgccatt tgtttgggct tacagaaaaa ctaaaggtcc agctaagtct    960
gattctgttg aattgccaga tggtttcgtt gaaagaacta gagatagagg tttggtttgg   1020
acttcttggg ctccacaatt gagaatttt tctcatgaat ccgtctgtgg tttcttgact   1080
cattgtggtt ctggttctat cgttgaaggt ttgatgtttg gtcacccatt gattatgttg   1140
ccaatctttg gtgaccaacc attgaacgct agattattgg aagataagca agtcggtatc   1200
gaaatcccaa gaaatgaaga gatggttgc ttgaccaaag aatctgttgc tagatctttg    1260
agatccgttg tcgttgaaaa agaaggtgaa atctacaagg ctaacgctag agaattgtcc    1320
aagatctaca acgataccaa ggtcgaaaaa gaatacgttt cccaattcgt tgactacttg    1380
gaaaagaatg ctagagctgt tgccattgat catgaatctt ga                      1422
```

<210> SEQ ID NO 6
<211> LENGTH: 297
<212> TYPE: PRT
<213> ORGANISM: Synechococcus sp.

<400> SEQUENCE: 6

Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
             35                  40                  45

Arg Leu Arg Pro Ile Leu Cys Leu Ala Ala Cys Glu Leu Ala Gly Gly
 50                  55                  60

Ser Val Glu Gln Ala Met Pro Thr Ala Cys Ala Leu Glu Met Ile His
 65                  70                  75                  80

Thr Met Ser Leu Ile His Asp Asp Leu Pro Ala Met Asp Asn Asp Asp
                 85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
        275                 280                 285

Ala Asp Phe Ile Thr Arg Arg Gln His
    290                 295

<210> SEQ ID NO 7
<211> LENGTH: 827
<212> TYPE: PRT
<213> ORGANISM: Zea mays

<400> SEQUENCE: 7

Met Val Leu Ser Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
            20                  25                  30

Asp Thr Val Ala Val Pro Ala Ala Ala Gly Arg Trp Arg Arg Ala Leu
        35                  40                  45

Ala Arg Ala Gln His Thr Ser Glu Ser Ala Ala Val Ala Lys Gly Ser
    50                  55                  60

Ser Leu Thr Pro Ile Val Arg Thr Asp Ala Glu Ser Arg Arg Thr Arg
65                  70                  75                  80

Trp Pro Thr Asp Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr

```
                100             105             110
Asp Thr Ala Trp Val Gly Leu Val Pro Arg Leu Asp Gly Glu Gly
            115             120             125

Pro Gln Phe Pro Ala Ala Val Arg Trp Ile Arg Asn Gln Leu Pro
            130             135             140

Asp Gly Ser Trp Gly Asp Ala Ala Leu Phe Ser Ala Tyr Asp Arg Leu
145             150             155             160

Ile Asn Thr Leu Ala Cys Val Val Thr Leu Thr Arg Trp Ser Leu Glu
                165             170             175

Pro Glu Met Arg Gly Arg Gly Leu Ser Phe Leu Gly Arg Asn Met Trp
            180             185             190

Lys Leu Ala Thr Glu Asp Glu Ser Met Pro Ile Gly Phe Glu Leu
            195             200             205

Ala Phe Pro Ser Leu Ile Glu Leu Ala Lys Ser Leu Gly Val His Asp
            210             215             220

Phe Pro Tyr Asp His Gln Ala Leu Gln Gly Ile Tyr Ser Ser Arg Glu
225             230             235             240

Ile Lys Met Lys Arg Ile Pro Lys Glu Val Met His Thr Val Pro Thr
                245             250             255

Ser Ile Leu His Ser Leu Glu Gly Met Pro Gly Leu Asp Trp Ala Lys
                260             265             270

Leu Leu Lys Leu Gln Ser Ser Asp Gly Ser Phe Leu Phe Ser Pro Ala
            275             280             285

Ala Thr Ala Tyr Ala Leu Met Asn Thr Gly Asp Asp Arg Cys Phe Ser
            290             295             300

Tyr Ile Asp Arg Thr Val Lys Lys Phe Asn Gly Gly Val Pro Asn Val
305             310             315             320

Tyr Pro Val Asp Leu Phe Glu His Ile Trp Ala Val Asp Arg Leu Glu
                325             330             335

Arg Leu Gly Ile Ser Arg Tyr Phe Gln Lys Glu Ile Glu Gln Cys Met
            340             345             350

Asp Tyr Val Asn Arg His Trp Thr Glu Asp Gly Ile Cys Trp Ala Arg
            355             360             365

Asn Ser Asp Val Lys Glu Val Asp Asp Thr Ala Met Ala Phe Arg Leu
            370             375             380

Leu Arg Leu His Gly Tyr Ser Val Ser Pro Asp Val Phe Lys Asn Phe
385             390             395             400

Glu Lys Asp Gly Glu Phe Phe Ala Phe Val Gly Gln Ser Asn Gln Ala
                405             410             415

Val Thr Gly Met Tyr Asn Leu Asn Arg Ala Ser Gln Ile Ser Phe Pro
                420             425             430

Gly Glu Asp Val Leu His Arg Ala Gly Ala Phe Ser Tyr Glu Phe Leu
            435             440             445

Arg Arg Lys Glu Ala Glu Gly Ala Leu Arg Asp Lys Trp Ile Ile Ser
            450             455             460

Lys Asp Leu Pro Gly Glu Val Val Tyr Thr Leu Asp Phe Pro Trp Tyr
465             470             475             480

Gly Asn Leu Pro Arg Val Glu Ala Arg Asp Tyr Leu Glu Gln Tyr Gly
                485             490             495

Gly Gly Asp Asp Val Trp Ile Gly Lys Thr Leu Tyr Arg Met Pro Leu
                500             505             510

Val Asn Asn Asp Val Tyr Leu Glu Leu Ala Arg Met Asp Phe Asn His
            515             520             525
```

```
Cys Gln Ala Leu His Gln Leu Glu Trp Gln Gly Leu Lys Arg Trp Tyr
            530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ser Val Tyr Glu Pro Cys Arg Ala
                565                 570                 575

Ala Glu Arg Leu Ala Trp Ala Arg Ala Ala Ile Leu Ala Asn Ala Val
                580                 585                 590

Ser Thr His Leu Arg Asn Ser Pro Ser Phe Arg Glu Arg Leu Glu His
            595                 600                 605

Ser Leu Arg Cys Arg Pro Ser Glu Glu Thr Asp Gly Ser Trp Phe Asn
610                 615                 620

Ser Ser Ser Gly Ser Asp Ala Val Leu Val Lys Ala Val Leu Arg Leu
625                 630                 635                 640

Thr Asp Ser Leu Ala Arg Glu Ala Gln Pro Ile His Gly Gly Asp Pro
                645                 650                 655

Glu Asp Ile Ile His Lys Leu Leu Arg Ser Ala Trp Ala Glu Trp Val
            660                 665                 670

Arg Glu Lys Ala Asp Ala Ala Asp Ser Val Cys Asn Gly Ser Ser Ala
            675                 680                 685

Val Glu Gln Glu Gly Ser Arg Met Val His Asp Lys Gln Thr Cys Leu
690                 695                 700

Leu Leu Ala Arg Met Ile Glu Ile Ser Ala Gly Arg Ala Ala Gly Glu
705                 710                 715                 720

Ala Ala Ser Glu Asp Gly Asp Arg Arg Ile Ile Gln Leu Thr Gly Ser
                725                 730                 735

Ile Cys Asp Ser Leu Lys Gln Lys Met Leu Val Ser Gln Asp Pro Glu
            740                 745                 750

Lys Asn Glu Glu Met Met Ser His Val Asp Asp Glu Leu Lys Leu Arg
            755                 760                 765

Ile Arg Glu Phe Val Gln Tyr Leu Leu Arg Leu Gly Glu Lys Lys Thr
770                 775                 780

Gly Ser Ser Glu Thr Arg Gln Thr Phe Leu Ser Ile Val Lys Ser Cys
785                 790                 795                 800

Tyr Tyr Ala Ala His Cys Pro Pro His Val Val Asp Arg His Ile Ser
                805                 810                 815

Arg Val Ile Phe Glu Pro Val Ser Ala Ala Lys
            820                 825

<210> SEQ ID NO 8
<211> LENGTH: 785
<212> TYPE: PRT
<213> ORGANISM: Arabidopsis thaliana

<400> SEQUENCE: 8

Met Ser Ile Asn Leu Arg Ser Ser Gly Cys Ser Ser Pro Ile Ser Ala
1               5                   10                  15

Thr Leu Glu Arg Gly Leu Asp Ser Glu Val Gln Thr Arg Ala Asn Asn
            20                  25                  30

Val Ser Phe Glu Gln Thr Lys Glu Lys Ile Arg Lys Met Leu Glu Lys
        35                  40                  45

Val Glu Leu Ser Val Ser Ala Tyr Asp Thr Ser Trp Val Ala Met Val
    50                  55                  60

Pro Ser Pro Ser Ser Gln Asn Ala Pro Leu Phe Pro Gln Cys Val Lys
```

```
            65                  70                  75                  80
Trp Leu Leu Asp Asn Gln His Glu Asp Gly Ser Trp Gly Leu Asp Asn
                    85                  90                  95

His Asp His Gln Ser Leu Lys Lys Asp Val Leu Ser Ser Thr Leu Ala
            100                 105                 110

Ser Ile Leu Ala Leu Lys Lys Trp Gly Ile Gly Glu Arg Gln Ile Asn
        115                 120                 125

Lys Gly Leu Gln Phe Ile Glu Leu Asn Ser Ala Leu Val Thr Asp Glu
    130                 135                 140

Thr Ile Gln Lys Pro Thr Gly Phe Asp Ile Ile Phe Pro Gly Met Ile
145                 150                 155                 160

Lys Tyr Ala Arg Asp Leu Asn Leu Thr Ile Pro Leu Gly Ser Glu Val
                165                 170                 175

Val Asp Asp Met Ile Arg Lys Arg Asp Leu Asp Leu Lys Cys Asp Ser
            180                 185                 190

Glu Lys Phe Ser Lys Gly Arg Glu Ala Tyr Leu Ala Tyr Val Leu Glu
        195                 200                 205

Gly Thr Arg Asn Leu Lys Asp Trp Asp Leu Ile Val Lys Tyr Gln Arg
    210                 215                 220

Lys Asn Gly Ser Leu Phe Asp Ser Pro Ala Thr Ala Ala Ala Phe
225                 230                 235                 240

Thr Gln Phe Gly Asn Asp Gly Cys Leu Arg Tyr Leu Cys Ser Leu Leu
                245                 250                 255

Gln Lys Phe Glu Ala Ala Val Pro Ser Val Tyr Pro Phe Asp Gln Tyr
            260                 265                 270

Ala Arg Leu Ser Ile Ile Val Thr Leu Glu Ser Leu Gly Ile Asp Arg
        275                 280                 285

Asp Phe Lys Thr Glu Ile Lys Ser Ile Leu Asp Glu Thr Tyr Arg Tyr
    290                 295                 300

Trp Leu Arg Gly Asp Glu Glu Ile Cys Leu Asp Leu Ala Thr Cys Ala
305                 310                 315                 320

Leu Ala Phe Arg Leu Leu Leu Ala His Gly Tyr Asp Val Ser Tyr Asp
                325                 330                 335

Pro Leu Lys Pro Phe Ala Glu Glu Ser Gly Phe Ser Asp Thr Leu Glu
            340                 345                 350

Gly Tyr Val Lys Asn Thr Phe Ser Val Leu Glu Leu Phe Lys Ala Ala
        355                 360                 365

Gln Ser Tyr Pro His Glu Ser Ala Leu Lys Lys Gln Cys Cys Trp Thr
    370                 375                 380

Lys Gln Tyr Leu Glu Met Glu Leu Ser Ser Trp Val Lys Thr Ser Val
385                 390                 395                 400

Arg Asp Lys Tyr Leu Lys Lys Glu Val Glu Asp Ala Leu Ala Phe Pro
                405                 410                 415

Ser Tyr Ala Ser Leu Glu Arg Ser Asp His Arg Arg Lys Ile Leu Asn
            420                 425                 430

Gly Ser Ala Val Glu Asn Thr Arg Val Thr Lys Thr Ser Tyr Arg Leu
        435                 440                 445

His Asn Ile Cys Thr Ser Asp Ile Leu Lys Leu Ala Val Asp Asp Phe
    450                 455                 460

Asn Phe Cys Gln Ser Ile His Arg Glu Glu Met Glu Arg Leu Asp Arg
465                 470                 475                 480

Trp Ile Val Glu Asn Arg Leu Gln Glu Leu Lys Phe Ala Arg Gln Lys
                485                 490                 495
```

Leu Ala Tyr Cys Tyr Phe Ser Gly Ala Ala Thr Leu Phe Ser Pro Glu
            500                 505                 510

Leu Ser Asp Ala Arg Ile Ser Trp Ala Lys Gly Val Leu Thr Thr
        515                 520                 525

Val Val Asp Asp Phe Phe Asp Val Gly Gly Ser Lys Glu Leu Glu
530                 535                 540

Asn Leu Ile His Leu Val Glu Lys Trp Asp Leu Asn Gly Val Pro Glu
545                 550                 555                 560

Tyr Ser Ser Glu His Val Glu Ile Ile Phe Ser Val Leu Arg Asp Thr
                565                 570                 575

Ile Leu Glu Thr Gly Asp Lys Ala Phe Thr Tyr Gln Gly Arg Asn Val
            580                 585                 590

Thr His His Ile Val Lys Ile Trp Leu Asp Leu Leu Lys Ser Met Leu
        595                 600                 605

Arg Glu Ala Glu Trp Ser Ser Asp Lys Ser Thr Pro Ser Leu Glu Asp
    610                 615                 620

Tyr Met Glu Asn Ala Tyr Ile Ser Phe Ala Leu Gly Pro Ile Val Leu
625                 630                 635                 640

Pro Ala Thr Tyr Leu Ile Gly Pro Pro Leu Pro Glu Lys Thr Val Asp
                645                 650                 655

Ser His Gln Tyr Asn Gln Leu Tyr Lys Leu Val Ser Thr Met Gly Arg
            660                 665                 670

Leu Leu Asn Asp Ile Gln Gly Phe Lys Arg Glu Ser Ala Glu Gly Lys
        675                 680                 685

Leu Asn Ala Val Ser Leu His Met Lys His Glu Arg Asp Asn Arg Ser
    690                 695                 700

Lys Glu Val Ile Ile Glu Ser Met Lys Gly Leu Ala Glu Arg Lys Arg
705                 710                 715                 720

Glu Glu Leu His Lys Leu Val Leu Glu Glu Lys Gly Ser Val Val Pro
                725                 730                 735

Arg Glu Cys Lys Glu Ala Phe Leu Lys Met Ser Lys Val Leu Asn Leu
            740                 745                 750

Phe Tyr Arg Lys Asp Asp Gly Phe Thr Ser Asn Asp Leu Met Ser Leu
        755                 760                 765

Val Lys Ser Val Ile Tyr Glu Pro Val Ser Leu Gln Lys Glu Ser Leu
    770                 775                 780

Thr
785

<210> SEQ ID NO 9
<211> LENGTH: 1542
<212> TYPE: DNA
<213> ORGANISM: Artificial Sequence
<220> FEATURE:
<223> OTHER INFORMATION: Codon-optimized KO

<400> SEQUENCE: 9
atggatgctg tgacgggttt gttaactgtc ccagcaaccg ctataactat tggtggaact    60
gctgtagcat tggcggtagc gctaatcttt tggtacctga atcctacac atcagctaga   120 agatcccaat caaatcatct tccaagagtg cctgaagtcc aggtgttcc attgttagga   180 aatctgttac aattgaagga gaaaaagcca tacatgactt ttacgagatg ggcagcgaca   240
tatggaccta tctatagtat caaaactggg gctacaagta tggttgtggt atcatctaat   300
gagatagcca aggaggcatt ggtgaccaga ttccaatcca tatctacaag gaacttatct   360

```
aaagccctga aagtacttac agcagataag acaatggtcg caatgtcaga ttatgatgat        420
tatcataaaa cagttaagag acacatactg accgccgtct tgggtcctaa tgcacagaaa        480
aagcatagaa ttcacagaga tatcatgatg gataacatat ctactcaact tcatgaattc        540
gtgaaaaaca acccgaaaca ggaagaggta gaccttagaa aaatctttca atctgagtta        600
ttcggcttag ctatgagaca agccttagga aaggatgttg aaagtttgta cgttgaagac        660
ctgaaaatca ctatgaatag agacgaaatc tttcaagtcc ttgttgttga tccaatgatg        720
ggagcaatcg atgttgattg gagagacttc tttccatacc taaagtgggt cccaaacaaa        780
aagttcgaaa atactattca acaaatgtac atcagaagag aagctgttat gaaatcttta        840
atcaaagagc acaaaagag aatagcgtca ggcgaaaagc taaatagtta tatcgattac        900
cttttatctg aagctcaaac tttaaccgat cagcaactat tgatgtcctt gtgggaacca        960
atcattgaat cttcagatac aacaatggtc acaacagaat gggcaatgta cgaattagct       1020
aaaaacccta aattgcaaga taggttgtac agagacatta agtccgtctg tggatctgaa       1080
aagataaccg aagagcatct atcacagctg ccttacatta cagctatttt ccacgaaaca       1140
ctgagaagac actcaccagt tcctatcatt cctctaagac atgtacatga agataccgtt       1200
ctaggcggct accatgttcc tgctggcaca gaacttgccg ttaacatcta cggttgcaac       1260
atggacaaaa acgtttggga aaatccagag gaatggaacc cagaaagatt catgaaagag       1320
aatgagacaa ttgattttca aaagacgatg gccttcggtg gtggtaagag agtttgtgct       1380
ggttccttgc aagccctttt aactgcatct attgggattg ggagaatggt tcaagagttc       1440
gaatggaaac tgaaggatat gactcaagag gaagtgaaca cgataggcct aactacacaa       1500
atgttaagac cattgagagc tattatcaaa cctaggatct aa                          1542
```

<210> SEQ ID NO 10
<211> LENGTH: 513
<212> TYPE: PRT
<213> ORGANISM: Stevia rebaudiana

<400> SEQUENCE: 10

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Tyr His Lys Thr
    130                 135                 140

Val Lys Arg His Ile Leu Thr Ala Val Leu Gly Pro Asn Ala Gln Lys
145                 150                 155                 160
```

Lys His Arg Ile His Arg Asp Ile Met Met Asp Asn Ile Ser Thr Gln
            165                 170                 175

Leu His Glu Phe Val Lys Asn Asn Pro Glu Gln Glu Val Asp Leu
        180                 185                 190

Arg Lys Ile Phe Gln Ser Glu Leu Phe Gly Leu Ala Met Arg Gln Ala
            195                 200                 205

Leu Gly Lys Asp Val Glu Ser Leu Tyr Val Glu Asp Leu Lys Ile Thr
            210                 215                 220

Met Asn Arg Asp Glu Ile Phe Gln Val Leu Val Asp Pro Met Met
225                 230                 235                 240

Gly Ala Ile Asp Val Asp Trp Arg Asp Phe Phe Pro Tyr Leu Lys Trp
            245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
            275                 280                 285

Ala Ser Gly Glu Lys Leu Asn Ser Tyr Ile Asp Tyr Leu Leu Ser Glu
            290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
            325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
            355                 360                 365

Gln Leu Pro Tyr Ile Thr Ala Ile Phe His Glu Thr Leu Arg Arg His
            370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
            405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
            435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
            485                 490                 495

Leu Thr Thr Gln Met Leu Arg Pro Leu Arg Ala Ile Ile Lys Pro Arg
            500                 505                 510

Ile

<210> SEQ ID NO 11
<211> LENGTH: 2139
<212> TYPE: DNA
<213> ORGANISM: Arabidopsis thaliana

<400> SEQUENCE: 11
atgtcttcct cttcctcttc cagtacctct atgattgatt tgatggctgc tattattaaa    60
ggtgaaccag ttatcgtctc cgacccagca aatgcctctg cttatgaatc agttgctgca   120

-continued

```
gaattgtctt caatgttgat cgaaaacaga caattcgcca tgatcgtaac tacatcaatc    180
gctgttttga tcggttgtat tgtcatgttg gtatggagaa gatccggtag tggtaattct    240
aaaagagtcg aacctttgaa accattagta attaagccaa gagaagaaga aatagatgac    300
ggtagaaaga aagttacaat attttcggt acccaaactg gtacagctga aggttttgca     360
aaagccttag gtgaagaagc taaggcaaga tacgaaaaga ctagattcaa gatagtcgat    420
ttggatgact atgccgctga tgacgatgaa tacgaagaaa gttgaagaa agaagatgtt     480 gcatttttct ttttggcaac ctatggtgac ggtgaaccaa ctgacaatgc agccagattc    540
tacaaatggt ttacagaggg taatgatcgt ggtgaatggt tgaaaaactt aaagtacggt    600
gttttcggtt tgggtaacag acaatacgaa catttcaaca aagttgcaaa ggttgtcgac    660
gatattttgg tcgaacaagg tgctcaaaga ttagtccaag taggtttggg tgacgatgac    720
caatgtatag aagatgactt tactgcctgg agagaagctt tgtggcctga attagacaca    780
atcttgagag aagaaggtga caccgccgtt gctaccccat atactgctgc agtattagaa    840
tacagagttt ccatccatga tagtgaagac gcaaagttta tgatatcac tttggccaat    900 ggtaacggtt atacagtttt cgatgcacaa caccccttaca aagctaacgt tgcagtcaag    960
agagaattac atacaccaga atccgacaga agttgtatac acttggaatt tgatatcgct   1020
ggttccggtt taaccatgaa gttgggtgac catgtaggtg ttttatgcga caatttgtct   1080
gaaactgttg atgaagcatt gagattgttg gatatgtccc ctgacactta ttttagtttg   1140
cacgctgaaa aagaagatgg tacaccaatt tccagttctt taccacctcc attccctcca   1200
tgtaacttaa gaacagcctt gaccagatac gcttgcttgt tatcatcccc taaaaagtcc   1260
gccttggttg ctttagccgc tcatgctagt gatcctactg aagcagaaag attgaaacac   1320
ttagcatctc cagccggtaa agatgaatat tcaaagtggg tagttgaatc tcaaagatca   1380
ttgttagaag ttatggcaga atttccatct gccaagcctc cattaggtgt cttctttgct   1440
ggtgtagcac ctagattgca accaagattc tactcaatca gttcttcacc taagatcgct   1500
gaaactagaa ttcatgttac atgtgcatta gtctacgaaa agatgccaac cggtagaatt   1560
cacaagggtg tatgctctac ttggatgaaa aatgctgttc cttacgaaaa atcagaaaag   1620
ttgttcttag gtagaccaat cttcgtaaga caatcaaact tcaagttgcc ttctgattca   1680
aaggttccaa taatcatgat aggtcctggt acaggtttag ccccattcag aggtttcttg   1740
caagaaagat tggctttagt tgaatctggt gtcgaattag gtccttcagt tttgttcttt   1800
ggttgtagaa acagaagaat ggatttcatc tatgaagaag aattgcaaag attcgtcgaa   1860
tctggtgcat tggccgaatt atctgtagct tttttcaagag aaggtccaac taaggaatac   1920
gttcaacata agatgatgga taaggcatcc gacatatgga acatgatcag tcaaggtgct   1980
tatttgtacg tttgcggtga cgcaaagggt atggccagag atgtccatag atctttgcac   2040
acaattgctc aagaacaagg ttccatggat agtaccaaag ctgaaggttt cgtaaagaac   2100
ttacaaactt ccggtagata cttgagagat gtctggtga                           2139
```

<210> SEQ ID NO 12
<211> LENGTH: 712
<212> TYPE: PRT
<213> ORGANISM: Arabidopsis thaliana

<400> SEQUENCE: 12

Met Ser Ser Ser Ser Ser Ser Ser Thr Ser Met Ile Asp Leu Met Ala
1               5                   10                  15

```
Ala Ile Ile Lys Gly Glu Pro Val Ile Val Ser Asp Pro Ala Asn Ala
            20                  25                  30

Ser Ala Tyr Glu Ser Val Ala Ala Glu Leu Ser Ser Met Leu Ile Glu
            35                  40                  45

Asn Arg Gln Phe Ala Met Ile Val Thr Thr Ser Ile Ala Val Leu Ile
 50                      55                  60

Gly Cys Ile Val Met Leu Val Trp Arg Arg Ser Gly Ser Gly Asn Ser
 65                  70                  75                  80

Lys Arg Val Glu Pro Leu Lys Pro Leu Val Ile Lys Pro Arg Glu Glu
                 85                  90                  95

Glu Ile Asp Asp Gly Arg Lys Lys Val Thr Ile Phe Phe Gly Thr Gln
            100                 105                 110

Thr Gly Thr Ala Glu Gly Phe Ala Lys Ala Leu Gly Glu Glu Ala Lys
            115                 120                 125

Ala Arg Tyr Glu Lys Thr Arg Phe Lys Ile Val Asp Leu Asp Asp Tyr
130                 135                 140

Ala Ala Asp Asp Asp Glu Tyr Glu Glu Lys Leu Lys Lys Glu Asp Val
145                 150                 155                 160

Ala Phe Phe Phe Leu Ala Thr Tyr Gly Asp Gly Glu Pro Thr Asp Asn
                165                 170                 175

Ala Ala Arg Phe Tyr Lys Trp Phe Thr Glu Gly Asn Asp Arg Gly Glu
            180                 185                 190

Trp Leu Lys Asn Leu Lys Tyr Gly Val Phe Gly Leu Gly Asn Arg Gln
            195                 200                 205

Tyr Glu His Phe Asn Lys Val Ala Lys Val Val Asp Asp Ile Leu Val
            210                 215                 220

Glu Gln Gly Ala Gln Arg Leu Val Gln Val Gly Leu Gly Asp Asp Asp
225                 230                 235                 240

Gln Cys Ile Glu Asp Asp Phe Thr Ala Trp Arg Glu Ala Leu Trp Pro
                245                 250                 255

Glu Leu Asp Thr Ile Leu Arg Glu Glu Gly Asp Thr Ala Val Ala Thr
            260                 265                 270

Pro Tyr Thr Ala Ala Val Leu Glu Tyr Arg Val Ser Ile His Asp Ser
            275                 280                 285

Glu Asp Ala Lys Phe Asn Asp Ile Thr Leu Ala Asn Gly Asn Gly Tyr
            290                 295                 300

Thr Val Phe Asp Ala Gln His Pro Tyr Lys Ala Asn Val Ala Val Lys
305                 310                 315                 320

Arg Glu Leu His Thr Pro Glu Ser Asp Arg Ser Cys Ile His Leu Glu
                325                 330                 335

Phe Asp Ile Ala Gly Ser Gly Leu Thr Met Lys Leu Gly Asp His Val
            340                 345                 350

Gly Val Leu Cys Asp Asn Leu Ser Glu Thr Val Asp Glu Ala Leu Arg
            355                 360                 365

Leu Leu Asp Met Ser Pro Asp Thr Tyr Phe Ser Leu His Ala Glu Lys
            370                 375                 380

Glu Asp Gly Thr Pro Ile Ser Ser Ser Leu Pro Pro Pro Phe Pro Pro
385                 390                 395                 400

Cys Asn Leu Arg Thr Ala Leu Thr Arg Tyr Ala Cys Leu Leu Ser Ser
                405                 410                 415

Pro Lys Lys Ser Ala Leu Val Ala Leu Ala Ala His Ala Ser Asp Pro
            420                 425                 430
```

```
Thr Glu Ala Glu Arg Leu Lys His Leu Ala Ser Pro Ala Gly Lys Asp
            435                 440                 445

Glu Tyr Ser Lys Trp Val Val Glu Ser Gln Arg Ser Leu Leu Glu Val
        450                 455                 460

Met Ala Glu Phe Pro Ser Ala Lys Pro Pro Leu Gly Val Phe Phe Ala
465                 470                 475                 480

Gly Val Ala Pro Arg Leu Gln Pro Arg Phe Tyr Ser Ile Ser Ser Ser
                485                 490                 495

Pro Lys Ile Ala Glu Thr Arg Ile His Val Thr Cys Ala Leu Val Tyr
            500                 505                 510

Glu Lys Met Pro Thr Gly Arg Ile His Lys Gly Val Cys Ser Thr Trp
        515                 520                 525

Met Lys Asn Ala Val Pro Tyr Glu Lys Ser Glu Lys Leu Phe Leu Gly
530                 535                 540

Arg Pro Ile Phe Val Arg Gln Ser Asn Phe Lys Leu Pro Ser Asp Ser
545                 550                 555                 560

Lys Val Pro Ile Ile Met Ile Gly Pro Gly Thr Gly Leu Ala Pro Phe
                565                 570                 575

Arg Gly Phe Leu Gln Glu Arg Leu Ala Leu Val Glu Ser Gly Val Glu
            580                 585                 590

Leu Gly Pro Ser Val Leu Phe Phe Gly Cys Arg Asn Arg Arg Met Asp
        595                 600                 605

Phe Ile Tyr Glu Glu Glu Leu Gln Arg Phe Val Glu Ser Gly Ala Leu
610                 615                 620

Ala Glu Leu Ser Val Ala Phe Ser Arg Glu Gly Pro Thr Lys Glu Tyr
625                 630                 635                 640

Val Gln His Lys Met Met Asp Lys Ala Ser Asp Ile Trp Asn Met Ile
                645                 650                 655

Ser Gln Gly Ala Tyr Leu Tyr Val Cys Gly Asp Ala Lys Gly Met Ala
            660                 665                 670

Arg Asp Val His Arg Ser Leu His Thr Ile Ala Gln Glu Gln Gly Ser
        675                 680                 685

Met Asp Ser Thr Lys Ala Glu Gly Phe Val Lys Asn Leu Gln Thr Ser
690                 695                 700

Gly Arg Tyr Leu Arg Asp Val Trp
705                 710

<210> SEQ ID NO 13
<211> LENGTH: 462
<212> TYPE: PRT
<213> ORGANISM: Oryza sativa

<400> SEQUENCE: 13

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95
```

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
            115                 120                 125

Val Phe His His Trp Ala Ala Ala Ala Leu Glu His Lys Val Pro
130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
            195                 200                 205

Ser Leu Thr Leu Ser Arg Ser Ser Leu Val Val Gly Arg Ser Cys Val
            210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
            245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
            275                 280                 285

Glu Lys Val His Glu Leu Ala Leu Gly Leu Glu Leu Ala Gly Thr Arg
            290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
            325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
            355                 360                 365

Phe Gly His Pro Leu Ile Met Leu Pro Ile Phe Gly Asp Gln Gly Pro
370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
            405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
            435                 440                 445

Tyr Ile Asp Gly Phe Ile Gln Gln Leu Arg Ser Tyr Lys Asp
            450                 455                 460

<210> SEQ ID NO 14
<211> LENGTH: 1503
<212> TYPE: DNA
<213> ORGANISM: Artificial Sequence
<220> FEATURE:
<223> OTHER INFORMATION: Codon-optimized stevia rebaudiana

<400> SEQUENCE: 14

```
atggaagcct cttacctata catttctatt ttgcttttac tggcatcata cctgttcacc      60
actcaactta gaaggaagag cgctaatcta ccaccaaccg tgtttccatc aataccaatc     120
attggacact tatacttact caaaaagcct ctttatagaa ctttagcaaa aattgccgct     180
aagtacggac caatactgca attacaactc ggctacagac gtgttctggt gatttcctca     240
ccatcagcag cagaagagtg ctttaccaat aacgatgtaa tcttcgcaaa tagacctaag     300
acattgtttg gcaaaatagt gggtggaaca tcccttggca gttatcccta cggcgatcaa     360
tggcgtaatc taaggagagt agcttctatc gaaatcctat cagttcatag gttgaacgaa     420
tttcatgata tcagagtgga tgagaacaga ttgttaatta gaaaacttag aagttcatct     480
tctcctgtta ctcttataac agtctttttat gctctaacat tgaacgtcat tatgagaatg     540
atctctggca aaagatattt cgacagtggg gatagagaat tggaggagga aggtaagaga     600
tttcgagaaa tcttagacga aacgttgctt ctagccggtg cttctaatgt tggcgactac     660
ttaccaatat tgaactggtt gggagttaag tctcttgaaa agaaattgat cgctttgcag     720
aaaaagagag atgacttttt ccagggtttg attgaacagg ttagaaaatc tcgtggtgct     780
aaagtaggca aagtagaaaa acgatgatc gaactcttat tatctttgca agagtcagaa     840
cctgagtact atacagatgc tatgataaga tctttttgtcc taggtctgct ggctgcaggt     900
agtgatactt cagcgggcac tatggaatgg gccatgagct tactggtcaa tcacccacat     960
gtattgaaga aagctcaagc tgaaatcgat agagttatcg gtaataacag attgattgac    1020
gagtcagaca ttggaaatat cccttacatc gggtgtatta tcaatgaaac tctaagactc    1080
tatccagcag ggccattgtt gttcccacat gaaagttctg ccgactgcgt tatttccggt    1140
tacaatatac ctagaggtac aatgttaatc gtaaaccaat gggcgattca tcacgatcct    1200
aaagtctggg atgatcctga aacctttaaa cctgaaagat ttcaaggatt agaaggaact    1260
agagatggtt tcaaacttat gccattcggt tctgggagaa gaggatgtcc aggtgaaggt    1320
ttggcaataa ggctgttagg gatgacacta ggctcagtga tccaatgttt tgattgggag    1380
agagtaggag atgagatggt tgacatgaca gaaggtttgg gtgtcacact tcctaaggcc    1440
gttccattag ttgccaaatg taagccacgt tccgaaatga ctaatctcct atccgaactt    1500
taa                                                                  1503
```

<210> SEQ ID NO 15
<211> LENGTH: 500
<212> TYPE: PRT
<213> ORGANISM: Stevia rebaudiana

<400> SEQUENCE: 15

```
Met Glu Ala Ser Tyr Leu Tyr Ile Ser Ile Leu Leu Leu Ala Ser
1               5                   10                  15

Tyr Leu Phe Thr Thr Gln Leu Arg Arg Lys Ser Ala Asn Leu Pro Pro
            20                  25                  30

Thr Val Phe Pro Ser Ile Pro Ile Ile Gly His Leu Tyr Leu Leu Lys
        35                  40                  45

Lys Pro Leu Tyr Arg Thr Leu Ala Lys Ile Ala Ala Lys Tyr Gly Pro
    50                  55                  60

Ile Leu Gln Leu Gln Leu Gly Tyr Arg Arg Val Leu Val Ile Ser Ser
65                  70                  75                  80

Pro Ser Ala Ala Glu Glu Cys Phe Thr Asn Asn Asp Val Ile Phe Ala
                85                  90                  95
```

```
Asn Arg Pro Lys Thr Leu Phe Gly Lys Ile Val Gly Thr Ser Leu
            100                 105                 110
Gly Ser Leu Ser Tyr Gly Asp Gln Trp Arg Asn Leu Arg Val Ala
        115                 120                 125
Ser Ile Glu Ile Leu Ser Val His Arg Leu Asn Glu Phe His Asp Ile
    130                 135                 140
Arg Val Asp Glu Asn Arg Leu Leu Ile Arg Lys Leu Arg Ser Ser Ser
145                 150                 155                 160
Ser Pro Val Thr Leu Ile Thr Val Phe Tyr Ala Leu Thr Leu Asn Val
                165                 170                 175
Ile Met Arg Met Ile Ser Gly Lys Arg Tyr Phe Asp Ser Gly Asp Arg
            180                 185                 190
Glu Leu Glu Glu Gly Lys Arg Phe Arg Glu Ile Leu Asp Glu Thr
        195                 200                 205
Leu Leu Leu Ala Gly Ala Ser Asn Val Gly Asp Tyr Leu Pro Ile Leu
    210                 215                 220
Asn Trp Leu Gly Val Lys Ser Leu Glu Lys Lys Leu Ile Ala Leu Gln
225                 230                 235                 240
Lys Lys Arg Asp Asp Phe Phe Gln Gly Leu Ile Glu Gln Val Arg Lys
                245                 250                 255
Ser Arg Gly Ala Lys Val Gly Lys Gly Arg Lys Thr Met Ile Glu Leu
            260                 265                 270
Leu Leu Ser Leu Gln Glu Ser Glu Pro Glu Tyr Tyr Thr Asp Ala Met
        275                 280                 285
Ile Arg Ser Phe Val Leu Gly Leu Leu Ala Ala Gly Ser Asp Thr Ser
    290                 295                 300
Ala Gly Thr Met Glu Trp Ala Met Ser Leu Leu Val Asn His Pro His
305                 310                 315                 320
Val Leu Lys Lys Ala Gln Ala Glu Ile Asp Arg Val Ile Gly Asn Asn
                325                 330                 335
Arg Leu Ile Asp Glu Ser Asp Ile Gly Asn Ile Pro Tyr Ile Gly Cys
            340                 345                 350
Ile Ile Asn Glu Thr Leu Arg Leu Tyr Pro Ala Gly Pro Leu Leu Phe
        355                 360                 365
Pro His Glu Ser Ser Ala Asp Cys Val Ile Ser Gly Tyr Asn Ile Pro
    370                 375                 380
Arg Gly Thr Met Leu Ile Val Asn Gln Trp Ala Ile His His Asp Pro
385                 390                 395                 400
Lys Val Trp Asp Asp Pro Glu Thr Phe Lys Pro Glu Arg Phe Gln Gly
                405                 410                 415
Leu Glu Gly Thr Arg Asp Gly Phe Lys Leu Met Pro Phe Gly Ser Gly
            420                 425                 430
Arg Arg Gly Cys Pro Gly Glu Gly Leu Ala Ile Arg Leu Leu Gly Met
        435                 440                 445
Thr Leu Gly Ser Val Ile Gln Cys Phe Asp Trp Glu Arg Val Gly Asp
    450                 455                 460
Glu Met Val Asp Met Thr Glu Gly Leu Gly Val Thr Leu Pro Lys Ala
465                 470                 475                 480
Val Pro Leu Val Ala Lys Cys Lys Pro Arg Ser Glu Met Thr Asn Leu
                485                 490                 495
Leu Ser Glu Leu
            500
```

<210> SEQ ID NO 16
<211> LENGTH: 2124
<212> TYPE: DNA
<213> ORGANISM: Stevia rebaudiana

<400> SEQUENCE: 16

```
atgcaatcta actccgtgaa gatttcgccg cttgatctgg taactgcgct gtttagcggc      60
aaggttttgg acacatcgaa cgcatcggaa tcgggagaat ctgctatgct gccgactata     120
gcgatgatta tggagaatcg tgagctgttg atgatactca aacgtcggt tgctgtattg      180
atcggatgcg ttgtcgtttt ggtgtggcgg agatcgtcta cgaagaagtc ggcgttggag     240
ccaccggtga ttgtggttcc gaagagagtg caagaggagg aagttgatga tggtaagaag     300
aaagttacgg ttttcttcgg cacccaaact ggaacagctg aaggcttcgc taaggcactt     360
gttgaggaag ctaaagctcg atatgaaaag gctgtcttta agtaattga tttggatgat      420
tatgctgctg atgacgatga gtatgaggag aaactaaaga aagaatcttt ggcctttttc     480
tttttggcta cgtatggaga tggtgagcca acagataatg ctgccagatt ttataaatgg     540
tttactgagg gagatgcgaa aggagaatgg cttaataagc ttcaatatgg agtatttggt     600
ttgggtaaca gacaatatga acattttaac aagatcgcaa aagtggttga tgatggtctt     660
gtagaacagg gtgcaaagcg tcttgttcct gttggacttg gagatgatga tcaatgtatt     720
gaagatgact tcaccgcatg gaaagagtta gtatggccgg agttggatca attacttcgt     780
gatgaggatg acacaactgt tgctactcca tacacagctg ctgttgcaga atatcgcgtt     840
gttttcatg aaaaaccaga cgcgcttttct gaagattata gttatacaaa tggccatgct      900
gttcatgatg ctcaacatcc atgcagatcc aacgtggctg tcaaaaagga acttcatagt     960
cctgaatctg accggtcttg cactcatctt gaatttgaca tctcgaacac cggactatca    1020
tatgaaactg gggaccatgt tggagtttac tgtgaaaact tgagtgaagt tgtgaatgat    1080
gctgaaagat tagtaggatt accaccagac acttactcct ccatccacac tgatagtgaa    1140
gacgggtcgc cacttggcgg agcctcattg ccgcctcctt tcccgccatg cactttaagg    1200
aaagcattga cgtgttatgc tgatgttttg agttctccca agaagtcggc tttgcttgca    1260
ctagctgctc atgccaccga tcccagtgaa gctgatagat tgaaatttct tgcatccccc    1320
gccggaaagg atgaatattc tcaatggata gttgcaagcc aaagaagtct ccttgaagtc    1380
atggaagcat tcccgtcagc taagccttca cttggtgttt tctttgcatc tgttgccccg    1440
cgcttacaac caagatacta ctctatttct tcctcaccca gatggcacc ggataggatt      1500
catgttacat gtgcattagt ctatgagaaa cacctgcag ccgcatcca caaggagtt       1560
tgttcaactt ggatgaagaa cgcagtgcct atgaccgaga gtcaagattg cagttgggcc    1620
ccaatatacg tccgaacatc caatttcaga ctaccatctg accctaaggt cccggttatc    1680
atgattggac ctggcactgg tttggctcct tttagaggtt ccttcaaga gcggttagct     1740
ttaaaggaag ccggaactga cctcggttta tccattttat tcttcggatg taggaatcgc    1800
aaagtggatt tcatatatga aaacgagctt aacaactttg tggagactgg tgctctttct    1860
gagcttattg ttgctttctc ccgtgaaggc ccgactaagg aatatgtgca acacaagatg    1920
agtgagaagg cttcggatat ctggaacttg ctttctgaag gagcatattt atacgtatgt    1980
ggtgatgcca aaggcatggc caaagatgta catcgaaccc tccacacaat tgtgcaagaa    2040
cagggatctc ttgactcgtc aaaggcagaa ctctacgtga agaatctaca aatgtcagga    2100
agatacctcc gtgacgtttg gtaa                                            2124
```

<210> SEQ ID NO 17
<211> LENGTH: 707
<212> TYPE: PRT
<213> ORGANISM: Stevia rebaudiana

<400> SEQUENCE: 17

```
Met Gln Ser Asn Ser Val Lys Ile Ser Pro Leu Asp Leu Val Thr Ala
1               5                   10                  15

Leu Phe Ser Gly Lys Val Leu Asp Thr Ser Asn Ala Ser Glu Ser Gly
            20                  25                  30

Glu Ser Ala Met Leu Pro Thr Ile Ala Met Ile Met Glu Asn Arg Glu
        35                  40                  45

Leu Leu Met Ile Leu Thr Thr Ser Val Ala Val Leu Ile Gly Cys Val
50                  55                  60

Val Val Leu Val Trp Arg Arg Ser Ser Thr Lys Lys Ser Ala Leu Glu
65                  70                  75                  80

Pro Pro Val Ile Val Pro Lys Arg Val Gln Glu Glu Val Asp
                85                  90                  95

Asp Gly Lys Lys Lys Val Thr Val Phe Phe Gly Thr Gln Thr Gly Thr
            100                 105                 110

Ala Glu Gly Phe Ala Lys Ala Leu Val Glu Glu Ala Lys Ala Arg Tyr
        115                 120                 125

Glu Lys Ala Val Phe Lys Val Ile Asp Leu Asp Asp Tyr Ala Ala Asp
    130                 135                 140

Asp Asp Glu Tyr Glu Glu Lys Leu Lys Lys Glu Ser Leu Ala Phe Phe
145                 150                 155                 160

Phe Leu Ala Thr Tyr Gly Asp Gly Glu Pro Thr Asp Asn Ala Ala Arg
                165                 170                 175

Phe Tyr Lys Trp Phe Thr Glu Gly Asp Ala Lys Gly Glu Trp Leu Asn
            180                 185                 190

Lys Leu Gln Tyr Gly Val Phe Gly Leu Gly Asn Arg Gln Tyr Glu His
        195                 200                 205

Phe Asn Lys Ile Ala Lys Val Val Asp Asp Gly Leu Val Glu Gln Gly
    210                 215                 220

Ala Lys Arg Leu Val Pro Val Gly Leu Gly Asp Asp Gln Cys Ile
225                 230                 235                 240

Glu Asp Asp Phe Thr Ala Trp Lys Glu Leu Val Trp Pro Glu Leu Asp
                245                 250                 255

Gln Leu Leu Arg Asp Glu Asp Thr Thr Val Ala Thr Pro Tyr Thr
            260                 265                 270

Ala Ala Val Ala Glu Tyr Arg Val Val Phe His Glu Lys Pro Asp Ala
        275                 280                 285

Leu Ser Glu Asp Tyr Ser Tyr Thr Asn Gly His Ala Val His Asp Ala
    290                 295                 300

Gln His Pro Cys Arg Ser Asn Val Ala Val Lys Lys Glu Leu His Ser
305                 310                 315                 320

Pro Glu Ser Asp Arg Ser Cys Thr His Leu Glu Phe Asp Ile Ser Asn
                325                 330                 335

Thr Gly Leu Ser Tyr Glu Thr Gly Asp His Val Gly Val Tyr Cys Glu
            340                 345                 350

Asn Leu Ser Glu Val Val Asn Asp Ala Glu Arg Leu Val Gly Leu Pro
        355                 360                 365

Pro Asp Thr Tyr Ser Ser Ile His Thr Asp Ser Glu Asp Gly Ser Pro
    370                 375                 380
```

Leu Gly Gly Ala Ser Leu Pro Pro Phe Pro Pro Cys Thr Leu Arg
385                 390                 395                 400

Lys Ala Leu Thr Cys Tyr Ala Asp Val Leu Ser Pro Lys Lys Ser
            405                 410                 415

Ala Leu Leu Ala Leu Ala Ala His Ala Thr Asp Pro Ser Glu Ala Asp
        420                 425                 430

Arg Leu Lys Phe Leu Ala Ser Pro Ala Gly Lys Asp Glu Tyr Ser Gln
        435                 440                 445

Trp Ile Val Ala Ser Gln Arg Ser Leu Leu Glu Val Met Glu Ala Phe
    450                 455                 460

Pro Ser Ala Lys Pro Ser Leu Gly Val Phe Phe Ala Ser Val Ala Pro
465                 470                 475                 480

Arg Leu Gln Pro Arg Tyr Tyr Ser Ile Ser Ser Ser Pro Lys Met Ala
            485                 490                 495

Pro Asp Arg Ile His Val Thr Cys Ala Leu Val Tyr Glu Lys Thr Pro
        500                 505                 510

Ala Gly Arg Ile His Lys Gly Val Cys Ser Thr Trp Met Lys Asn Ala
        515                 520                 525

Val Pro Met Thr Glu Ser Gln Asp Cys Ser Trp Ala Pro Ile Tyr Val
530                 535                 540

Arg Thr Ser Asn Phe Arg Leu Pro Ser Asp Pro Lys Val Pro Val Ile
545                 550                 555                 560

Met Ile Gly Pro Gly Thr Gly Leu Ala Pro Phe Arg Gly Phe Leu Gln
            565                 570                 575

Glu Arg Leu Ala Leu Lys Glu Ala Gly Thr Asp Leu Gly Leu Ser Ile
        580                 585                 590

Leu Phe Phe Gly Cys Arg Asn Arg Lys Val Asp Phe Ile Tyr Glu Asn
        595                 600                 605

Glu Leu Asn Asn Phe Val Glu Thr Gly Ala Leu Ser Glu Leu Ile Val
    610                 615                 620

Ala Phe Ser Arg Glu Gly Pro Thr Lys Glu Tyr Val Gln His Lys Met
625                 630                 635                 640

Ser Glu Lys Ala Ser Asp Ile Trp Asn Leu Leu Ser Glu Gly Ala Tyr
            645                 650                 655

Leu Tyr Val Cys Gly Asp Ala Lys Gly Met Ala Lys Asp Val His Arg
        660                 665                 670

Thr Leu His Thr Ile Val Gln Glu Gln Gly Ser Leu Asp Ser Ser Lys
        675                 680                 685

Ala Glu Leu Tyr Val Lys Asn Leu Gln Met Ser Gly Arg Tyr Leu Arg
    690                 695                 700

Asp Val Trp
705

<210> SEQ ID NO 18
<211> LENGTH: 2133
<212> TYPE: DNA
<213> ORGANISM: Artificial Sequence
<220> FEATURE:
<223> OTHER INFORMATION: Codon optimized

<400> SEQUENCE: 18
atgcaatcag attcagtcaa agtctctcca tttgatttgg tttccgctgc tatgaatggc      60
aaggcaatgg aaaagttgaa cgctagtgaa tctgaagatc caacaacatt gcctgcacta     120
aagatgctag ttgaaaatag agaattgttg acactgttca caacttcctt cgcagttctt     180

```
attgggtgtc ttgtatttct aatgtggaga cgttcatcct ctaaaaagct ggtacaagat    240
ccagttccac aagttatcgt tgtaaagaag aaagagaagg agtcagaggt tgatgacggg    300
aaaaagaaag tttctatttt ctacggcaca caaacaggaa ctgccgaagg ttttgctaaa    360
gcattagtcg aggaagcaaa agtgagatat gaaaagacct ctttcaaggt tatcgatcta    420
gatgactacg ctgcagatga tgatgaatat gaggaaaaac tgaaaaagga atccttagcc    480
ttcttcttct tggccacata cggtgatggt gaacctactg ataatgctgc taacttctac    540
aagtggttca cagaaggcga cgataaaggt gaatggctga aaagttaca atacggagta    600
tttggtttag gtaacagaca atatgaacat ttcaacaaga tcgctattgt agttgatgat    660
aaacttactg aaatgggagc caaaagatta gtaccagtag gattagggga tgatgatcag    720
tgtatagaag atgacttcac cgcctggaag gaattggtat ggccagaatt ggatcaactt    780
ttaagggacg aagatgatac ttctgtgact accccataca ctgcagccgt attggagtac    840
agagtggttt accatgataa accagcagac tcatatgctg aagatcaaac ccatacaaac    900
ggtcatgttg ttcatgatgc acagcatcct tcaagatcta atgtggcttt caaaaaggaa    960
ctacacacct ctcaatcaga taggtcttgt actcacttag aattcgatat ttctcacaca   1020
ggactgtctt acgaaactgg cgatcacgtt ggcgtttatt ccgagaactt gtccgaagtt   1080
gtcgatgaag cactaaaact gttagggtta tcaccagaca catacttctc agtccatgct   1140
gataaggagg atgggacacc tatcggtggt gcttcactac caccacccttt tcctccttgc   1200
acattgagag acgctctaac cagatacgca gatgtcttat cctcacctaa aaaggtagct   1260
ttgctggcat tggctgctca tgctagtgat cctagtgaag ccgataggtt aaagttcctg   1320
gcttcaccag ccggaaaaga tgaatatgca caatggatcg tcgccaacca acgttctttg   1380
ctagaagtga tgcaaagttt tccatctgcc aagcctccat taggtgtgtt cttcgcagca   1440
gtagctccac gtttacaacc aagatactac tctatcagtt catctcctaa gatgtctcct   1500
aacagaatac atgttacatg tgctttggtg tacgagacta ctccagcagg cagaattcac   1560
agaggattgt gttcaacctg gatgaaaaat gctgtccctt taacagagtc acctgattgc   1620
tctcaagcat ccattttcgt tagaacatca aatttcagac ttccagtgga tccaaaagtt   1680
ccagtcatta tgataggacc aggcactggt cttgccccat tcagggggctt tcttcaagag   1740
agattggcct tgaaggaatc tggtacagaa ttgggttctt ctatcttttt ctttggttgc   1800
cgtaatagaa aagttgactt tatctacgag gacgagctta caattttgt tgagacagga   1860
gcattgtcag aattgatcgt cgcatttttca agagaaggga ctgccaaaga gtacgttcag   1920
cacaagatga gtcaaaaagc ctccgatata tggaaacttc taagtgaagg tgcctatctt   1980
tatgtctgtg gcgatgcaaa gggcatggcc aaggatgtcc atagaactct gcatacaatt   2040
gttcaggaac aagggagtct ggattcttcc aaggctgaat tgtacgtcaa aaacttacag   2100
atgtctggaa gatacttaag agatgtttgg taa                                2133
```

<210> SEQ ID NO 19  
<211> LENGTH: 710  
<212> TYPE: PRT  
<213> ORGANISM: Stevia rebaudiana

<400> SEQUENCE: 19

```
Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
```

```
            20                  25                  30
Asp Pro Thr Thr Leu Pro Ala Leu Lys Met Leu Val Glu Asn Arg Glu
        35                  40                  45
Leu Leu Thr Leu Phe Thr Thr Ser Phe Ala Val Leu Ile Gly Cys Leu
    50                  55                  60
Val Phe Leu Met Trp Arg Arg Ser Ser Lys Lys Leu Val Gln Asp
65                  70                  75                  80
Pro Val Pro Gln Val Ile Val Val Lys Lys Glu Lys Glu Ser Glu
                85                  90                  95
Val Asp Asp Gly Lys Lys Val Ser Ile Phe Tyr Gly Thr Gln Thr
            100                 105                 110
Gly Thr Ala Glu Gly Phe Ala Lys Ala Leu Val Glu Glu Ala Lys Val
            115                 120                 125
Arg Tyr Glu Lys Thr Ser Phe Lys Val Ile Asp Leu Asp Asp Tyr Ala
        130                 135                 140
Ala Asp Asp Asp Glu Tyr Glu Glu Lys Leu Lys Lys Glu Ser Leu Ala
145                 150                 155                 160
Phe Phe Phe Leu Ala Thr Tyr Gly Asp Gly Glu Pro Thr Asp Asn Ala
            165                 170                 175
Ala Asn Phe Tyr Lys Trp Phe Thr Glu Gly Asp Lys Gly Glu Trp
        180                 185                 190
Leu Lys Lys Leu Gln Tyr Gly Val Phe Gly Leu Gly Asn Arg Gln Tyr
        195                 200                 205
Glu His Phe Asn Lys Ile Ala Ile Val Val Asp Asp Lys Leu Thr Glu
        210                 215                 220
Met Gly Ala Lys Arg Leu Val Pro Val Gly Leu Gly Asp Asp Asp Gln
225                 230                 235                 240
Cys Ile Glu Asp Asp Phe Thr Ala Trp Lys Glu Leu Val Trp Pro Glu
            245                 250                 255
Leu Asp Gln Leu Leu Arg Asp Glu Asp Asp Thr Ser Val Thr Thr Pro
        260                 265                 270
Tyr Thr Ala Ala Val Leu Glu Tyr Arg Val Val Tyr His Asp Lys Pro
        275                 280                 285
Ala Asp Ser Tyr Ala Glu Asp Gln Thr His Thr Asn Gly His Val Val
        290                 295                 300
His Asp Ala Gln His Pro Ser Arg Ser Asn Val Ala Phe Lys Lys Glu
305                 310                 315                 320
Leu His Thr Ser Gln Ser Asp Arg Ser Cys Thr His Leu Glu Phe Asp
            325                 330                 335
Ile Ser His Thr Gly Leu Ser Tyr Glu Thr Gly Asp His Val Gly Val
            340                 345                 350
Tyr Ser Glu Asn Leu Ser Glu Val Asp Glu Ala Leu Lys Leu Leu
        355                 360                 365
Gly Leu Ser Pro Asp Thr Tyr Phe Ser Val His Ala Asp Lys Glu Asp
        370                 375                 380
Gly Thr Pro Ile Gly Gly Ala Ser Leu Pro Pro Phe Pro Pro Cys
385                 390                 395                 400
Thr Leu Arg Asp Ala Leu Thr Arg Tyr Ala Asp Val Leu Ser Ser Pro
            405                 410                 415
Lys Lys Val Ala Leu Leu Ala Leu Ala Ala His Ala Ser Asp Pro Ser
            420                 425                 430
Glu Ala Asp Arg Leu Lys Phe Leu Ala Ser Pro Ala Gly Lys Asp Glu
        435                 440                 445
```

Tyr Ala Gln Trp Ile Val Ala Asn Gln Arg Ser Leu Leu Glu Val Met
450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
                500                 505                 510

Thr Thr Pro Ala Gly Arg Ile His Arg Gly Leu Cys Ser Thr Trp Met
                515                 520                 525

Lys Asn Ala Val Pro Leu Thr Glu Ser Pro Asp Cys Ser Gln Ala Ser
530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
                580                 585                 590

Ser Ser Ile Phe Phe Gly Cys Arg Asn Arg Lys Val Asp Phe Ile
                595                 600                 605

Tyr Glu Asp Glu Leu Asn Asn Phe Val Glu Thr Gly Ala Leu Ser Glu
                610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
                675                 680                 685

Ser Ser Lys Ala Glu Leu Tyr Val Lys Asn Leu Gln Met Ser Gly Arg
690                 695                 700

Tyr Leu Arg Asp Val Trp
705                 710

<210> SEQ ID NO 20
<211> LENGTH: 511
<212> TYPE: PRT
<213> ORGANISM: Rubus suavissimus

<400> SEQUENCE: 20

Met Ala Thr Leu Leu Glu His Phe Gln Ala Met Pro Phe Ala Ile Pro
1               5                   10                  15

Ile Ala Leu Ala Ala Leu Ser Trp Leu Phe Leu Phe Tyr Ile Lys Val
                20                  25                  30

Ser Phe Phe Ser Asn Lys Ser Ala Gln Ala Lys Leu Pro Pro Val Pro
                35                  40                  45

Val Val Pro Gly Leu Pro Val Ile Gly Asn Leu Leu Gln Leu Lys Glu
            50                  55                  60

Lys Lys Pro Tyr Gln Thr Phe Thr Arg Trp Ala Glu Glu Tyr Gly Pro
65                  70                  75                  80

Ile Tyr Ser Ile Arg Thr Gly Ala Ser Thr Met Val Val Leu Asn Thr
                85                  90                  95

Thr Gln Val Ala Lys Glu Ala Met Val Thr Arg Tyr Leu Ser Ile Ser

```
                    100                 105                 110
Thr Arg Lys Leu Ser Asn Ala Leu Lys Ile Leu Thr Ala Asp Lys Cys
            115                 120                 125

Met Val Ala Ile Ser Asp Tyr Asn Asp Phe His Lys Met Ile Lys Arg
130                 135                 140

Tyr Ile Leu Ser Asn Val Leu Gly Pro Ser Ala Gln Lys Arg His Arg
145                 150                 155                 160

Ser Asn Arg Asp Thr Leu Arg Ala Asn Val Cys Ser Arg Leu His Ser
                165                 170                 175

Gln Val Lys Asn Ser Pro Arg Glu Ala Val Asn Phe Arg Arg Val Phe
            180                 185                 190

Glu Trp Glu Leu Phe Gly Ile Ala Leu Lys Gln Ala Phe Gly Lys Asp
        195                 200                 205

Ile Glu Lys Pro Ile Tyr Val Glu Leu Gly Thr Thr Leu Ser Arg
    210                 215                 220

Asp Glu Ile Phe Lys Val Leu Val Leu Asp Ile Met Glu Gly Ala Ile
225                 230                 235                 240

Glu Val Asp Trp Arg Asp Phe Phe Pro Tyr Leu Arg Trp Ile Pro Asn
                245                 250                 255

Thr Arg Met Glu Thr Lys Ile Gln Arg Leu Tyr Phe Arg Arg Lys Ala
            260                 265                 270

Val Met Thr Ala Leu Ile Asn Glu Gln Lys Lys Arg Ile Ala Ser Gly
        275                 280                 285

Glu Glu Ile Asn Cys Tyr Ile Asp Phe Leu Leu Lys Glu Gly Lys Thr
    290                 295                 300

Leu Thr Met Asp Gln Ile Ser Met Leu Leu Trp Glu Thr Val Ile Glu
305                 310                 315                 320

Thr Ala Asp Thr Thr Met Val Thr Thr Glu Trp Ala Met Tyr Glu Val
                325                 330                 335

Ala Lys Asp Ser Lys Arg Gln Asp Arg Leu Tyr Gln Glu Ile Gln Lys
            340                 345                 350

Val Cys Gly Ser Glu Met Val Thr Glu Glu Tyr Leu Ser Gln Leu Pro
        355                 360                 365

Tyr Leu Asn Ala Val Phe His Glu Thr Leu Arg Lys His Ser Pro Ala
    370                 375                 380

Ala Leu Val Pro Leu Arg Tyr Ala His Glu Asp Thr Gln Leu Gly Gly
385                 390                 395                 400

Tyr Tyr Ile Pro Ala Gly Thr Glu Ile Ala Ile Asn Ile Tyr Gly Cys
                405                 410                 415

Asn Met Asp Lys His Gln Trp Glu Ser Pro Glu Glu Trp Lys Pro Glu
            420                 425                 430

Arg Phe Leu Asp Pro Lys Phe Asp Pro Met Asp Leu Tyr Lys Thr Met
        435                 440                 445

Ala Phe Gly Ala Gly Lys Arg Val Cys Ala Gly Ser Leu Gln Ala Met
    450                 455                 460

Leu Ile Ala Cys Pro Thr Ile Gly Arg Leu Val Gln Glu Phe Glu Trp
465                 470                 475                 480

Lys Leu Arg Asp Gly Glu Glu Asn Val Asp Thr Val Gly Leu Thr
                485                 490                 495

Thr His Lys Arg Tyr Pro Met His Ala Ile Leu Lys Pro Arg Ser
            500                 505                 510

<210> SEQ ID NO 21
```

<211> LENGTH: 523
<212> TYPE: PRT
<213> ORGANISM: Rubus suavissimus

<400> SEQUENCE: 21

```
Met Glu Val Thr Val Ala Ser Ser Val Ala Leu Ser Leu Val Phe Ile
1               5                   10                  15

Ser Ile Val Val Arg Trp Ala Trp Ser Val Val Asn Trp Val Trp Phe
            20                  25                  30

Lys Pro Lys Lys Leu Glu Arg Phe Leu Arg Glu Gln Gly Leu Lys Gly
        35                  40                  45

Asn Ser Tyr Arg Phe Leu Tyr Gly Asp Met Lys Glu Asn Ser Ile Leu
    50                  55                  60

Leu Lys Gln Ala Arg Ser Lys Pro Met Asn Leu Ser Thr Ser His Asp
65                  70                  75                  80

Ile Ala Pro Gln Val Thr Pro Phe Val Asp Gln Thr Val Lys Ala Tyr
                85                  90                  95

Gly Lys Asn Ser Phe Asn Trp Val Gly Pro Ile Pro Arg Val Asn Ile
            100                 105                 110

Met Asn Pro Glu Asp Leu Lys Asp Val Leu Thr Lys Asn Val Asp Phe
        115                 120                 125

Val Lys Pro Ile Ser Asn Pro Leu Ile Lys Leu Leu Ala Thr Gly Ile
    130                 135                 140

Ala Ile Tyr Glu Gly Glu Lys Trp Thr Lys His Arg Arg Ile Ile Asn
145                 150                 155                 160

Pro Thr Phe His Ser Glu Arg Leu Lys Arg Met Leu Pro Ser Phe His
                165                 170                 175

Gln Ser Cys Asn Glu Met Val Lys Glu Trp Glu Ser Leu Val Ser Lys
            180                 185                 190

Glu Gly Ser Ser Cys Glu Leu Asp Val Trp Pro Phe Leu Glu Asn Met
        195                 200                 205

Ser Ala Asp Val Ile Ser Arg Thr Ala Phe Gly Thr Ser Tyr Lys Lys
    210                 215                 220

Gly Gln Lys Ile Phe Glu Leu Leu Arg Glu Gln Val Ile Tyr Val Thr
225                 230                 235                 240

Lys Gly Phe Gln Ser Phe Tyr Ile Pro Gly Trp Arg Phe Leu Pro Thr
                245                 250                 255

Lys Met Asn Lys Arg Met Asn Glu Ile Asn Glu Glu Ile Lys Gly Leu
            260                 265                 270

Ile Arg Gly Ile Ile Ile Asp Arg Glu Gln Ile Ile Lys Ala Gly Glu
        275                 280                 285

Glu Thr Asn Asp Asp Leu Leu Gly Ala Leu Met Glu Ser Asn Leu Lys
    290                 295                 300

Asp Ile Arg Glu His Gly Lys Asn Asn Lys Asn Val Gly Met Ser Ile
305                 310                 315                 320

Glu Asp Val Ile Gln Glu Cys Lys Leu Phe Tyr Phe Ala Gly Gln Glu
                325                 330                 335

Thr Thr Ser Val Leu Leu Ala Trp Thr Met Val Leu Leu Gly Gln Asn
            340                 345                 350

Gln Asn Trp Gln Asp Arg Ala Arg Gln Glu Val Leu Gln Val Phe Gly
        355                 360                 365

Ser Ser Lys Pro Asp Phe Asp Gly Leu Ala His Leu Lys Val Val Thr
    370                 375                 380

Met Ile Leu Leu Glu Val Leu Arg Leu Tyr Pro Pro Val Ile Glu Leu
```

```
385                 390                 395                 400
Ile Arg Thr Ile His Lys Lys Thr Gln Leu Gly Lys Leu Ser Leu Pro
                405                 410                 415
Glu Gly Val Glu Val Arg Leu Pro Thr Leu Leu Ile His His Asp Lys
            420                 425                 430
Glu Leu Trp Gly Asp Asp Ala Asn Gln Phe Asn Pro Glu Arg Phe Ser
        435                 440                 445
Glu Gly Val Ser Lys Ala Thr Lys Asn Arg Leu Ser Phe Phe Pro Phe
    450                 455                 460
Gly Ala Gly Pro Arg Ile Cys Ile Gly Gln Asn Phe Ser Met Met Glu
465                 470                 475                 480
Ala Lys Leu Ala Leu Ala Leu Ile Leu Gln His Phe Thr Phe Glu Leu
                485                 490                 495
Ser Pro Ser His Ala His Ala Pro Ser His Arg Ile Thr Leu Gln Pro
            500                 505                 510
Gln Tyr Gly Val Arg Ile Ile Leu His Arg Arg
        515                 520

<210> SEQ ID NO 22
<211> LENGTH: 701
<212> TYPE: PRT
<213> ORGANISM: Siraitia grosvenorii

<400> SEQUENCE: 22

Met Lys Val Ser Pro Phe Glu Phe Met Ser Ala Ile Ile Lys Gly Arg
1               5                   10                  15
Met Asp Pro Ser Asn Ser Ser Phe Glu Ser Thr Gly Glu Val Ala Ser
            20                  25                  30
Val Ile Phe Glu Asn Arg Glu Leu Val Ala Ile Leu Thr Thr Ser Ile
        35                  40                  45
Ala Val Met Ile Gly Cys Phe Val Leu Met Trp Arg Arg Ala Gly
    50                  55                  60
Ser Arg Lys Val Lys Asn Val Glu Leu Pro Lys Pro Leu Ile Val His
65                  70                  75                  80
Glu Pro Glu Pro Glu Val Glu Asp Gly Lys Lys Val Ser Ile Phe
                85                  90                  95
Phe Gly Thr Gln Thr Gly Thr Ala Glu Gly Phe Ala Lys Ala Leu Ala
            100                 105                 110
Asp Glu Ala Lys Ala Arg Tyr Glu Lys Ala Thr Phe Arg Val Val Asp
        115                 120                 125
Leu Asp Asp Tyr Ala Ala Asp Asp Gln Tyr Glu Lys Leu Lys
    130                 135                 140
Asn Glu Ser Phe Ala Val Phe Leu Leu Ala Thr Tyr Gly Asp Gly Glu
145                 150                 155                 160
Pro Thr Asp Asn Ala Ala Arg Phe Tyr Lys Trp Phe Ala Glu Gly Lys
                165                 170                 175
Glu Arg Gly Glu Trp Leu Gln Asn Leu His Tyr Ala Val Phe Gly Leu
            180                 185                 190
Gly Asn Arg Gln Tyr Glu His Phe Asn Lys Ile Ala Lys Val Ala Asp
        195                 200                 205
Glu Leu Leu Glu Ala Gln Gly Gly Asn Arg Leu Val Lys Val Gly Leu
    210                 215                 220
Gly Asp Asp Asp Gln Cys Ile Glu Asp Asp Phe Ser Ala Trp Arg Glu
225                 230                 235                 240
```

```
Ser Leu Trp Pro Glu Leu Asp Met Leu Leu Arg Asp Glu Asp Ala
            245                 250                 255

Thr Thr Val Thr Thr Pro Tyr Thr Ala Ala Val Leu Glu Tyr Arg Val
            260                 265                 270

Val Phe His Asp Ser Ala Asp Val Ala Ala Glu Asp Lys Ser Trp Ile
        275                 280                 285

Asn Ala Asn Gly His Ala Val His Asp Ala Gln His Pro Phe Arg Ser
        290                 295                 300

Asn Val Val Arg Lys Glu Leu His Thr Ser Ala Ser Asp Arg Ser
305                 310                 315                 320

Cys Ser His Leu Glu Phe Asn Ile Ser Gly Ser Ala Leu Asn Tyr Glu
                325                 330                 335

Thr Gly Asp His Val Gly Val Tyr Cys Glu Asn Leu Thr Glu Thr Val
                340                 345                 350

Asp Glu Ala Leu Asn Leu Leu Gly Leu Ser Pro Glu Thr Tyr Phe Ser
            355                 360                 365

Ile Tyr Thr Asp Asn Glu Asp Gly Thr Pro Leu Gly Gly Ser Ser Leu
    370                 375                 380

Pro Pro Pro Phe Pro Ser Cys Thr Leu Arg Thr Ala Leu Thr Arg Tyr
385                 390                 395                 400

Ala Asp Leu Leu Asn Ser Pro Lys Lys Ser Ala Leu Leu Ala Leu Ala
                405                 410                 415

Ala His Ala Ser Asn Pro Val Glu Ala Asp Arg Leu Arg Tyr Leu Ala
                420                 425                 430

Ser Pro Ala Gly Lys Asp Glu Tyr Ala Gln Ser Val Ile Gly Ser Gln
            435                 440                 445

Lys Ser Leu Leu Glu Val Met Ala Glu Phe Pro Ser Ala Lys Pro Pro
450                 455                 460

Leu Gly Val Phe Phe Ala Ala Val Ala Pro Arg Leu Gln Pro Arg Phe
465                 470                 475                 480

Tyr Ser Ile Ser Ser Ser Pro Arg Met Ala Pro Ser Arg Ile His Val
                485                 490                 495

Thr Cys Ala Leu Val Tyr Asp Lys Met Pro Thr Gly Arg Ile His Lys
            500                 505                 510

Gly Val Cys Ser Thr Trp Met Lys Asn Ser Val Pro Met Glu Lys Ser
            515                 520                 525

His Glu Cys Ser Trp Ala Pro Ile Phe Val Arg Gln Ser Asn Phe Lys
            530                 535                 540

Leu Pro Ala Glu Ser Lys Val Pro Ile Ile Met Val Gly Pro Gly Thr
545                 550                 555                 560

Gly Leu Ala Pro Phe Arg Gly Phe Leu Gln Glu Arg Leu Ala Leu Lys
                565                 570                 575

Glu Ser Gly Val Glu Leu Gly Pro Ser Ile Leu Phe Phe Gly Cys Arg
            580                 585                 590

Asn Arg Arg Met Asp Tyr Ile Tyr Glu Asp Glu Leu Asn Asn Phe Val
            595                 600                 605

Glu Thr Gly Ala Leu Ser Glu Leu Val Ile Ala Phe Ser Arg Glu Gly
        610                 615                 620

Pro Thr Lys Glu Tyr Val Gln His Lys Met Ala Glu Lys Ala Ser Asp
625                 630                 635                 640

Ile Trp Asn Leu Ile Ser Glu Gly Ala Tyr Leu Tyr Val Cys Gly Asp
                645                 650                 655

Ala Lys Gly Met Ala Lys Asp Val His Arg Thr Leu His Thr Ile Met
```

-continued

```
               660                 665                 670
Gln Glu Gln Gly Ser Leu Asp Ser Ser Lys Ala Glu Ser Met Val Lys
            675                 680                 685

Asn Leu Gln Met Asn Gly Arg Tyr Leu Arg Asp Val Trp
            690                 695                 700
```